US011521745B2

(12) United States Patent
Berthelot et al.

(10) Patent No.: US 11,521,745 B2
(45) Date of Patent: Dec. 6, 2022

(54) METHOD FOR DETECTING ABNORMAL VALUES OF A BIOMARKER

(71) Applicants: Universite Paris-SUD, Orsay (FR); Universite De Paris, Paris (FR); Institut National De Sport De L'Expertise Et De La Performance, Paris (FR); Centre National de la Recherche Scientifique (CNRS), Paris (FR)

(72) Inventors: Geoffroy Berthelot, Chelles (FR); Jérôme Dedecker, Bourg la Reine (FR); Guillaume Sauliere, Vincennes (FR)

(73) Assignees: Université Paris-Saclay; Université Paris Cité; Institut National Du Sport De L'Expertise Et De La Performance; Centre National de la Recherche Scientifique (CNRS)

( * ) Notice: Subject to any disclaimer, the term of this patent is extended or adjusted under 35 U.S.C. 154(b) by 305 days.

(21) Appl. No.: 16/763,815

(22) PCT Filed: Nov. 14, 2018

(86) PCT No.: PCT/EP2018/081271
§ 371 (c)(1),
(2) Date: May 13, 2020

(87) PCT Pub. No.: WO2019/096869
PCT Pub. Date: May 23, 2019

(65) Prior Publication Data

US 2020/0388388 A1 Dec. 10, 2020

(30) Foreign Application Priority Data

Nov. 14, 2017 (EP) .................................... 17306583

(51) Int. Cl.
*G01N 33/48* (2006.01)
*G01N 33/50* (2006.01)
(Continued)

(52) U.S. Cl.
CPC ............ *G16H 50/20* (2018.01); *A61B 5/004* (2013.01); *A61B 5/0004* (2013.01);
(Continued)

(58) Field of Classification Search
CPC ...... G16H 50/20; G16H 50/30; A61B 5/0004; A61B 5/004; A61B 5/7264; G06F 17/18
(Continued)

(56) References Cited

U.S. PATENT DOCUMENTS

2012/0328594 A1* 12/2012 McKenna .......... G01N 33/6893 424/94.4
2018/0020947 A1* 1/2018 Cistola ................ A61B 5/4866 600/411

FOREIGN PATENT DOCUMENTS

WO 2014033433 A1 3/2014
WO WO-2014033433 A1 * 3/2014 ......... G05B 23/0235
(Continued)

OTHER PUBLICATIONS

International Search Report for Application No. PCT/EP2018/081271 dated Jan. 16, 2019, 3 pages.
(Continued)

*Primary Examiner* — Tanmay K Shah

(57) ABSTRACT

The invention proposes a new method for monitoring a health event in a mammal, comprising detecting at least one abnormal value within a series of values related to at least one biomarker, based on appropriate Z-scores.

13 Claims, 17 Drawing Sheets

E1 — E2 — ES — ET
ET → E3 → E4 → E5 → E6 → E7

(51) Int. Cl.
*G16H 50/20* (2018.01)
*G16H 50/30* (2018.01)
*G06F 17/18* (2006.01)
*A61B 5/00* (2006.01)

(52) U.S. Cl.
CPC ............ *A61B 5/7264* (2013.01); *G06F 17/18* (2013.01); *G16H 50/30* (2018.01)

(58) Field of Classification Search
USPC ............................................................ 702/19
See application file for complete search history.

(56) References Cited

FOREIGN PATENT DOCUMENTS

| | | | | | |
|---|---|---|---|---|---|
| WO | 2017068146 | A1 | | 4/2017 | |
| WO | WO-2017068146 | A1 | * | 4/2017 | ............. G06F 19/00 |
| WO | WO-2017179073 | A1 | * | 10/2017 | ........... A61B 5/0006 |

OTHER PUBLICATIONS

Sauliere, et al., "Z-scores-based methods and their application to biological monitoring: an example in professional soccer players," Database accession No. NLM29149240, Database Medline [Online] US National Library of Medicine (NLM), Nov. 15, 2017, pp. 1-2, XP055450846, Bethesda, MD, US, abstract only.

Sottas, et al., "Bayesian detection of abnormal values in longitudinal biomarkers with an application to T/E ratio," Biostatistics, Jun. 19, 2006, pp. 285-296, vol. 8, No. 2, XP055450738.

* cited by examiner detected values (%)
a→n = 4
b→n = 5
c→n = 6
d→n = 7
e→n = 8
f→n = 9
g→n = 10
h→n = 11
i→n = 12
j→n = 13
k→n = 14
l→n = 15
detected values (%)
A
B
C
D
μ
μ

A
Density
0.8
0.7
0.6
0.5
0.4
0.3
0.2
0.1
0
0
2
4
6
8
10
12
$T_n$
serum iron
simulated
B
Density
ferritin
simulated

FIG. 5

| | ferritin | serum ion | red blood cells | hemoglobin | hematocrit | total |
|---|---|---|---|---|---|---|
| **method1** | | | | | | |
| usual (n) | 715 | 695 | | | | **1410** |
| unusual (n) | 42 | 62 | | | | **104** |
| unusual (%) | 5.55 | 8.19 | | | | **6.87** |
| **(multivariate)** | | | | | | |
| usual (n) | | 661 | | | | **661** |
| unusual (n) | | 49 | | | | **49** |
| unusual (%) | | 6.90 | | | | **6.9** |
| **method2** | | | | | | |
| usual (n) | 674 | 707 | | | | **1381** |
| unusual (n) | 83 | 50 | | | | **133** |
| unusual (%) | 10.96 | 6.61 | | | | **8.78** |
| **method3** | | | | | | |
| usual (n) | | | 577 | 588 | 593 | **1758** |
| unusual (n) | | | 41 | 38 | 35 | **114** |
| unusual (%) | | | 6.63 | 6.07 | 5.57 | **6.09** |

A
B
C
D
E
F
serum iron
ferritin
semester
semester
semester
semester
semester
semester G
H
I
J
K
L
erythrocyte
serum iron
ferritin
summer
winter
serum iron
ferritin
semester

FIG. 8

Table 1 - Method 1 in dimension 1

| n \ level | 0.8 | 0.81 | 0.82 | 0.83 | 0.84 | 0.85 | 0.86 | 0.87 | 0.88 | 0.89 | 0.9 | 0.91 | 0.92 | 0.93 |
|---|---|---|---|---|---|---|---|---|---|---|---|---|---|---|
| 3 | 9.52 | 10.025 | 10.585 | 11.21 | 11.914 | 12.715 | 13.625 | 14.681 | 15.909 | 17.359 | 19.098 | 21.226 | 23.894 | 27.303 |
| 4 | 4.3032 | 4.4237 | 4.5547 | 4.6962 | 4.8504 | 5.0199 | 5.2066 | 5.4143 | 5.6463 | 5.9097 | 6.2101 | 6.558 | 6.9692 | 7.4641 |
| 5 | 3.4826 | 3.554 | 3.6302 | 3.7123 | 3.8006 | 3.8963 | 4.0011 | 4.1155 | 4.2412 | 4.3823 | 4.5416 | 4.7223 | 4.9301 | 5.1747 |
| 6 | 3.1863 | 3.2402 | 3.2974 | 3.3587 | 3.4246 | 3.4955 | 3.5721 | 3.6556 | 3.7473 | 3.8485 | 3.9612 | 4.0885 | 4.2339 | 4.4036 |
| 7 | 3.0456 | 3.0906 | 3.1385 | 3.1893 | 3.2436 | 3.302 | 3.3648 | 3.4331 | 3.5077 | 3.5897 | 3.6806 | 3.7823 | 3.8979 | 4.0319 |
| 8 | 2.9686 | 3.0084 | 3.0503 | 3.0949 | 3.1424 | 3.1933 | 3.2483 | 3.3075 | 3.3719 | 3.4424 | 3.5209 | 3.6082 | 3.7073 | 3.8213 |
| 9 | 2.924 | 2.9601 | 2.9983 | 3.0389 | 3.082 | 3.1279 | 3.1776 | 3.2308 | 3.2885 | 3.3516 | 3.4216 | 3.4994 | 3.5874 | 3.6879 |
| 10 | 2.896 | 2.9296 | 2.9651 | 3.0025 | 3.0423 | 3.0849 | 3.1304 | 3.1793 | 3.2329 | 3.2912 | 3.3553 | 3.4264 | 3.5064 | 3.5976 |
| 11 | 2.8795 | 2.9111 | 2.9445 | 2.9799 | 3.0172 | 3.0571 | 3.1 | 3.1459 | 3.1956 | 3.2498 | 3.3095 | 3.3757 | 3.4502 | 3.5351 |
| 12 | 2.8688 | 2.8989 | 2.9306 | 2.9641 | 2.9996 | 3.0374 | 3.0779 | 3.1212 | 3.1682 | 3.2196 | 3.2758 | 3.338 | 3.4082 | 3.4879 |
| 13 | 2.8636 | 2.8925 | 2.923 | 2.955 | 2.989 | 3.0253 | 3.0641 | 3.1057 | 3.1507 | 3.1997 | 3.2533 | 3.3126 | 3.3792 | 3.455 |
| 14 | 2.8607 | 2.8887 | 2.9181 | 2.9492 | 2.982 | 3.0169 | 3.0542 | 3.0944 | 3.1374 | 3.1844 | 3.2357 | 3.2924 | 3.3561 | 3.4285 |
| 15 | 2.8599 | 2.887 | 2.9157 | 2.9457 | 2.9775 | 3.0113 | 3.0474 | 3.0863 | 3.1281 | 3.1735 | 3.2228 | 3.2775 | 3.3391 | 3.4083 |
| 16 | 2.8614 | 2.8878 | 2.9155 | 2.9447 | 2.9757 | 3.0086 | 3.0437 | 3.0811 | 3.1216 | 3.1657 | 3.2137 | 3.2666 | 3.3259 | 3.393 |
| 17 | 2.8633 | 2.8891 | 2.9161 | 2.9447 | 2.9749 | 3.0068 | 3.041 | 3.0775 | 3.1169 | 3.1597 | 3.2063 | 3.2579 | 3.3153 | 3.3803 |
| 18 | 2.8663 | 2.8915 | 2.9181 | 2.946 | 2.9755 | 3.0069 | 3.0401 | 3.0758 | 3.1141 | 3.1558 | 3.2012 | 3.2516 | 3.3076 | 3.371 |
| 19 | 2.87 | 2.8948 | 2.9208 | 2.9482 | 2.9772 | 3.0079 | 3.0406 | 3.0755 | 3.1131 | 3.154 | 3.1986 | 3.2476 | 3.3023 | 3.3642 |
| 20 | 2.8739 | 2.8983 | 2.9237 | 2.9506 | 2.979 | 3.0091 | 3.041 | 3.0752 | 3.1121 | 3.152 | 3.1955 | 3.2436 | 3.2971 | 3.3574 |

| 0.94 | 0.95 | 0.96 | 0.97 | 0.98 | 0.99 | 0.991 | 0.992 | 0.993 | 0.994 | 0.995 | 0.996 | 0.997 | 0.998 | 0.999 |
|---|---|---|---|---|---|---|---|---|---|---|---|---|---|---|
| 31.87 | 38.249 | 47.85 | 63.857 | 95.762 | 191.68 | 213.02 | 239.56 | 273.84 | 319.24 | 383.11 | 479.59 | 638.83 | 958.71 | 1910.1 |
| 8.0774 | 8.8642 | 9.9315 | 11.492 | 14.1 | 19.969 | 21.053 | 22.341 | 23.863 | 25.809 | 28.284 | 31.614 | 36.523 | 44.703 | 63.067 |
| 5.4703 | 5.8389 | 6.3218 | 6.9951 | 8.0532 | 10.223 | 10.596 | 11.03 | 11.544 | 12.164 | 12.927 | 13.941 | 15.356 | 17.589 | 22.205 |
| 4.605 | 4.8511 | 5.1669 | 5.5958 | 6.2499 | 7.526 | 7.7361 | 7.9806 | 8.2615 | 8.6028 | 9.0193 | 9.5577 | 10.293 | 11.432 | 13.642 |
| 4.1901 | 4.3811 | 4.6234 | 4.9495 | 5.4346 | 6.3529 | 6.5012 | 6.6731 | 6.8712 | 7.1058 | 7.39 | 7.7494 | 8.2416 | 8.9818 | 10.384 |
| 3.9548 | 4.1161 | 4.3182 | 4.5866 | 4.983 | 5.7129 | 5.8279 | 5.9612 | 6.1155 | 6.2982 | 6.5196 | 6.8005 | 7.1673 | 7.7218 | 8.7553 |
| 3.8057 | 3.9468 | 4.122 | 4.3552 | 4.6941 | 5.3097 | 5.407 | 5.517 | 5.6425 | 5.7921 | 5.9729 | 6.2004 | 6.5052 | 6.9447 | 7.7652 |
| 3.7039 | 3.8312 | 3.989 | 4.1969 | 4.498 | 5.0377 | 5.1225 | 5.2191 | 5.3293 | 5.4585 | 5.6141 | 5.8077 | 6.0606 | 6.4296 | 7.1043 |
| 3.6335 | 3.751 | 3.8965 | 4.0877 | 4.3631 | 4.8524 | 4.9282 | 5.0152 | 5.1132 | 5.2285 | 5.3664 | 5.5379 | 5.7617 | 6.0877 | 6.6811 |
| 3.5804 | 3.6902 | 3.8264 | 4.0038 | 4.2576 | 4.7054 | 4.7751 | 4.8534 | 4.9438 | 5.0493 | 5.175 | 5.3284 | 5.533 | 5.8253 | 6.3487 |
| 3.5425 | 3.6463 | 3.7742 | 3.9408 | 4.1786 | 4.5968 | 4.662 | 4.7344 | 4.817 | 4.9139 | 5.0291 | 5.1704 | 5.3596 | 5.6288 | 6.1081 |
| 3.5124 | 3.6115 | 3.7337 | 3.8918 | 4.1171 | 4.5097 | 4.5703 | 4.6385 | 4.7156 | 4.806 | 4.914 | 5.0477 | 5.2212 | 5.4739 | 5.9134 |
| 3.4885 | 3.5841 | 3.7005 | 3.8521 | 4.0678 | 4.4425 | 4.4999 | 4.5641 | 4.6374 | 4.7227 | 4.824 | 4.949 | 5.1117 | 5.3436 | 5.7456 |
| 3.4704 | 3.5618 | 3.6745 | 3.8198 | 4.0265 | 4.3849 | 4.4394 | 4.5016 | 4.5708 | 4.6514 | 4.7475 | 4.8659 | 5.0199 | 5.241 | 5.6247 |
| 3.4555 | 3.5445 | 3.6534 | 3.7937 | 3.993 | 4.3368 | 4.3887 | 4.4473 | 4.5143 | 4.5923 | 4.6839 | 4.7977 | 4.9454 | 5.1558 | 5.5188 |
| 3.444 | 3.5302 | 3.6358 | 3.7719 | 3.9649 | 4.2965 | 4.3477 | 4.4035 | 4.468 | 4.5419 | 4.6293 | 4.7382 | 4.8797 | 5.0827 | 5.4308 |
| 3.4355 | 3.5194 | 3.622 | 3.7545 | 3.9408 | 4.2624 | 4.3118 | 4.366 | 4.4283 | 4.5005 | 4.5857 | 4.6918 | 4.8285 | 5.0199 | 5.358 |
| 3.4272 | 3.5095 | 3.61 | 3.7391 | 3.9208 | 4.2308 | 4.2785 | 4.332 | 4.3926 | 4.4624 | 4.5446 | 4.6462 | 4.7782 | 4.9652 | 5.2895 |

FIG. 9

Table 2 - Method 2

| $n$ \ level | 0.8 | 0.81 | 0.82 | 0.83 | 0.84 | 0.85 | 0.86 | 0.87 | 0.88 | 0.89 | 0.9 | 0.91 | 0.92 | 0.93 |
|---|---|---|---|---|---|---|---|---|---|---|---|---|---|---|
| 3 | 9.52 | 10.025 | 10.585 | 11.21 | 11.914 | 12.715 | 13.625 | 14.681 | 15.909 | 17.359 | 19.098 | 21.226 | 23.894 | 27.303 |
| 4 | 5.341 | 5.4875 | 5.6449 | 5.816 | 6.0035 | 6.2081 | 6.4338 | 6.6853 | 6.9675 | 7.2863 | 7.6509 | 8.0756 | 8.5754 | 9.1789 |
| 5 | 4.541 | 4.628 | 4.721 | 4.821 | 4.9293 | 5.0462 | 5.1743 | 5.3147 | 5.4701 | 5.6436 | 5.8392 | 6.063 | 6.3224 | 6.6275 |
| 6 | 4.225 | 4.2918 | 4.3624 | 4.437 | 4.5171 | 4.6036 | 4.6965 | 4.7973 | 4.9077 | 5.0303 | 5.1676 | 5.322 | 5.4989 | 5.7049 |
| 7 | 4.0271 | 4.0849 | 4.1459 | 4.2104 | 4.2791 | 4.3523 | 4.4304 | 4.515 | 4.6068 | 4.7075 | 4.8188 | 4.9429 | 5.0833 | 5.2452 |
| 8 | 3.8912 | 3.9429 | 3.9973 | 4.0548 | 4.1158 | 4.1809 | 4.2503 | 4.3255 | 4.4061 | 4.4943 | 4.5915 | 4.6992 | 4.8205 | 4.9593 |
| 9 | 3.7934 | 3.8409 | 3.8907 | 3.9433 | 3.9987 | 4.0576 | 4.1205 | 4.1882 | 4.2613 | 4.3412 | 4.4286 | 4.5251 | 4.6341 | 4.7575 |
| 10 | 3.722 | 3.7657 | 3.8118 | 3.8603 | 3.9119 | 3.9665 | 4.0248 | 4.0872 | 4.1548 | 4.2278 | 4.3084 | 4.3974 | 4.4967 | 4.6092 |
| 11 | 3.6694 | 3.7106 | 3.7538 | 3.7994 | 3.8477 | 3.8989 | 3.9535 | 4.0121 | 4.0749 | 4.143 | 4.2179 | 4.3005 | 4.3927 | 4.4976 |
| 12 | 3.6288 | 3.6678 | 3.7086 | 3.7519 | 3.7975 | 3.8458 | 3.8971 | 3.9522 | 4.0115 | 4.0756 | 4.1459 | 4.223 | 4.3088 | 4.4066 |
| 13 | 3.5977 | 3.6349 | 3.6741 | 3.7153 | 3.7586 | 3.8046 | 3.8535 | 3.906 | 3.9622 | 4.0231 | 4.0894 | 4.1626 | 4.2444 | 4.3369 |
| 14 | 3.5738 | 3.6096 | 3.6472 | 3.6867 | 3.7281 | 3.7722 | 3.8192 | 3.8692 | 3.9229 | 3.9809 | 4.0445 | 4.1145 | 4.1922 | 4.2802 |
| 15 | 3.555 | 3.5897 | 3.6259 | 3.6638 | 3.7038 | 3.7463 | 3.7913 | 3.8394 | 3.8913 | 3.9472 | 4.0083 | 4.0752 | 4.1497 | 4.2338 |
| 16 | 3.5396 | 3.573 | 3.608 | 3.6447 | 3.6833 | 3.7242 | 3.7677 | 3.8142 | 3.8641 | 3.9181 | 3.977 | 4.0414 | 4.113 | 4.1939 |
| 17 | 3.5281 | 3.5604 | 3.5943 | 3.63 | 3.6675 | 3.7072 | 3.7495 | 3.7947 | 3.8432 | 3.8954 | 3.9522 | 4.0147 | 4.084 | 4.1619 |
| 18 | 3.5187 | 3.5502 | 3.5834 | 3.6182 | 3.6547 | 3.6934 | 3.7344 | 3.7783 | 3.8252 | 3.8759 | 3.9311 | 3.9917 | 4.0592 | 4.1353 |
| 19 | 3.5118 | 3.5426 | 3.5747 | 3.6085 | 3.6441 | 3.6818 | 3.7219 | 3.7644 | 3.8102 | 3.8596 | 3.9131 | 3.9721 | 4.0374 | 4.1112 |
| 20 | 3.5062 | 3.5363 | 3.5679 | 3.6011 | 3.6359 | 3.6727 | 3.7119 | 3.7536 | 3.798 | 3.8464 | 3.8987 | 3.9561 | 4.0199 | 4.0917 |

| 0.94 | 0.95 | 0.96 | 0.97 | 0.98 | 0.99 | 0.991 | 0.992 | 0.993 | 0.994 | 0.995 | 0.996 | 0.997 | 0.998 | 0.999 |
|---|---|---|---|---|---|---|---|---|---|---|---|---|---|---|
| 31.87 | 38.249 | 47.85 | 63.857 | 95.762 | 191.68 | 213.02 | 239.56 | 273.84 | 319.24 | 383.11 | 479.59 | 638.83 | 958.71 | 1910.1 |
| 9.93 | 10.894 | 12.194 | 14.091 | 17.272 | 24.436 | 25.78 | 27.361 | 29.256 | 31.585 | 34.63 | 38.721 | 44.677 | 54.763 | 77.59 |
| 6.9945 | 7.4522 | 8.0514 | 8.8913 | 10.217 | 12.926 | 13.391 | 13.935 | 14.572 | 15.35 | 16.315 | 17.59 | 19.361 | 22.217 | 27.923 |
| 5.951 | 6.2531 | 6.6412 | 7.1726 | 7.9859 | 9.5624 | 9.8298 | 10.135 | 10.49 | 10.915 | 11.442 | 12.114 | 13.042 | 14.464 | 17.215 |
| 5.4353 | 5.6655 | 5.9579 | 6.3522 | 6.9418 | 8.0555 | 8.238 | 8.446 | 8.6906 | 8.9774 | 9.3296 | 9.7796 | 10.376 | 11.292 | 13.03 |
| 5.1209 | 5.3155 | 5.5581 | 5.8786 | 6.3532 | 7.2285 | 7.3706 | 7.5312 | 7.7157 | 7.9346 | 8.2021 | 8.534 | 8.9837 | 9.6453 | 10.888 |
| 4.9009 | 5.0726 | 5.2844 | 5.5632 | 5.9681 | 6.6975 | 6.8133 | 6.944 | 7.0952 | 7.2727 | 7.4906 | 7.7576 | 8.1136 | 8.6441 | 9.6004 |
| 4.7392 | 4.8943 | 5.0851 | 5.3346 | 5.6943 | 6.3305 | 6.4311 | 6.5438 | 6.674 | 6.8249 | 7.0067 | 7.2322 | 7.5371 | 7.9726 | 8.7679 |
| 4.618 | 4.7615 | 4.9373 | 5.1668 | 5.4933 | 6.0679 | 6.1569 | 6.258 | 6.374 | 6.5093 | 6.6709 | 6.87 | 7.1304 | 7.5156 | 8.2099 |
| 4.5192 | 4.6525 | 4.8155 | 5.0279 | 5.3292 | 5.8552 | 5.9361 | 6.0283 | 6.133 | 6.256 | 6.3998 | 6.5804 | 6.8173 | 7.1599 | 7.7643 |
| 4.4434 | 4.5686 | 4.7228 | 4.9217 | 5.2035 | 5.6927 | 5.7673 | 5.8518 | 5.9482 | 6.0608 | 6.1952 | 6.3606 | 6.5764 | 6.8886 | 7.4384 |
| 4.3813 | 4.5002 | 4.6459 | 4.8336 | 5.0995 | 5.56 | 5.6306 | 5.7104 | 5.8008 | 5.9049 | 6.0306 | 6.1852 | 6.3857 | 6.6733 | 7.1744 |
| 4.3304 | 4.4446 | 4.5834 | 4.7624 | 5.0147 | 5.4483 | 5.5146 | 5.5893 | 5.6729 | 5.7719 | 5.8881 | 6.0317 | 6.2188 | 6.4858 | 6.9568 |
| 4.287 | 4.3968 | 4.5303 | 4.7008 | 4.9415 | 5.3542 | 5.4173 | 5.4885 | 5.5677 | 5.6614 | 5.7718 | 5.9093 | 6.0855 | 6.3364 | 6.7712 |
| 4.2518 | 4.3575 | 4.486 | 4.6511 | 4.8816 | 5.2783 | 5.3389 | 5.4063 | 5.4834 | 5.5721 | 5.6771 | 5.806 | 5.9744 | 6.2141 | 6.6308 |
| 4.2224 | 4.3245 | 4.4484 | 4.607 | 4.8299 | 5.2115 | 5.2692 | 5.3342 | 5.4071 | 5.4919 | 5.5923 | 5.715 | 5.8768 | 6.1041 | 6.4971 |
| 4.196 | 4.2953 | 4.4154 | 4.5696 | 4.7859 | 5.1528 | 5.2089 | 5.2717 | 5.3429 | 5.4254 | 5.5221 | 5.6404 | 5.7968 | 6.0171 | 6.3928 |
| 4.1739 | 4.2702 | 4.3873 | 4.5372 | 4.7467 | 5.1031 | 5.1575 | 5.2173 | 5.2853 | 5.3634 | 5.4561 | 5.57 | 5.7186 | 5.928 | 6.2899 |

FIG. 10

Table 3 - Method 3

| $n$ | $n_1$ | $n_2$ | level 0.8 | 0.81 | 0.82 | 0.83 | 0.84 | 0.85 | 0.86 | 0.87 | 0.88 | 0.89 | 0.9 | 0.91 | 0.92 | 0.93 |
|---|---|---|---|---|---|---|---|---|---|---|---|---|---|---|---|---|
| 4 | 2 | 2 | 6.3139 | 6.653 | 7.0279 | 7.4476 | 7.9177 | 8.4504 | 9.0609 | 9.7676 | 10.586 | 11.552 | 12.71 | 14.129 | 15.908 | 18.175 |
| 5 | 2 | 3 | 4.3042 | 4.4248 | 4.5553 | 4.6968 | 4.8516 | 5.0204 | 5.2057 | 5.4123 | 5.6444 | 5.9073 | 6.2083 | 6.5551 | 6.967 | 7.461 |
| 6 | 3 | 3 | 3.7404 | 3.8154 | 3.8958 | 3.9823 | 4.0753 | 4.1768 | 4.2871 | 4.4076 | 4.541 | 4.6897 | 4.8577 | 5.0484 | 5.2687 | 5.5285 |
| 6 | 2 | 4 | 3.4819 | 3.5533 | 3.6296 | 3.7118 | 3.8002 | 3.8958 | 4.0001 | 4.1144 | 4.241 | 4.3822 | 4.5405 | 4.7216 | 4.9304 | 5.1755 |
| 7 | 3 | 4 | 3.3502 | 3.406 | 3.4651 | 3.5282 | 3.5961 | 3.6689 | 3.7476 | 3.8336 | 3.9277 | 4.0321 | 4.1484 | 4.2796 | 4.4301 | 4.6052 |
| 7 | 2 | 5 | 3.1868 | 3.2407 | 3.2981 | 3.3592 | 3.4251 | 3.496 | 3.5727 | 3.6561 | 3.7476 | 3.8485 | 3.961 | 4.0877 | 4.2334 | 4.4033 |
| 8 | 4 | 4 | 3.1641 | 3.2099 | 3.2585 | 3.3104 | 3.3654 | 3.4246 | 3.4888 | 3.5584 | 3.6343 | 3.7179 | 3.8105 | 3.9146 | 4.0328 | 4.1694 |
| 8 | 3 | 5 | 3.1603 | 3.2066 | 3.2557 | 3.3079 | 3.3636 | 3.4231 | 3.4876 | 3.5574 | 3.6334 | 3.7171 | 3.8098 | 3.914 | 4.032 | 4.1682 |
| 8 | 2 | 6 | 3.0463 | 3.0913 | 3.139 | 3.1898 | 3.2443 | 3.3025 | 3.3655 | 3.4338 | 3.508 | 3.5897 | 3.6805 | 3.7823 | 3.8979 | 4.0314 |
| 9 | 4 | 5 | 3.059 | 3.0992 | 3.1418 | 3.1873 | 3.2356 | 3.2871 | 3.3425 | 3.4025 | 3.4679 | 3.5395 | 3.6187 | 3.7073 | 3.8072 | 3.9222 |
| 9 | 3 | 6 | 3.0547 | 3.0954 | 3.1382 | 3.1839 | 3.2327 | 3.2849 | 3.341 | 3.4017 | 3.4676 | 3.5396 | 3.6191 | 3.7078 | 3.8082 | 3.9235 |
| 9 | 2 | 7 | 2.9692 | 3.0087 | 3.0507 | 3.0953 | 3.1429 | 3.1941 | 3.2489 | 3.3082 | 3.3728 | 3.4437 | 3.5217 | 3.6092 | 3.7081 | 3.8216 |
| 10 | 5 | 5 | 2.9973 | 3.034 | 3.0727 | 3.1136 | 3.1572 | 3.2036 | 3.2534 | 3.3071 | 3.3655 | 3.4292 | 3.4999 | 3.5785 | 3.6673 | 3.7685 |
| 10 | 4 | 6 | 2.9962 | 3.033 | 3.0717 | 3.1129 | 3.1563 | 3.2028 | 3.2529 | 3.3068 | 3.3654 | 3.4294 | 3.5 | 3.5786 | 3.6672 | 3.7689 |
| 10 | 3 | 7 | 2.9909 | 3.0278 | 3.0668 | 3.108 | 3.1519 | 3.1989 | 3.2494 | 3.3038 | 3.3627 | 3.4271 | 3.4979 | 3.577 | 3.6661 | 3.768 |
| 10 | 2 | 8 | 2.9232 | 2.9593 | 2.9974 | 3.0377 | 3.0808 | 3.1269 | 3.1765 | 3.2299 | 3.2878 | 3.3511 | 3.421 | 3.4987 | 3.5866 | 3.6869 |
| 11 | 5 | 6 | 2.9574 | 2.9914 | 3.0272 | 3.065 | 3.1052 | 3.148 | 3.1939 | 3.2433 | 3.2969 | 3.3554 | 3.4199 | 3.4917 | 3.5722 | 3.6641 |
| 11 | 4 | 7 | 2.9558 | 2.9898 | 3.0257 | 3.0637 | 3.104 | 3.147 | 3.1929 | 3.2425 | 3.2961 | 3.3547 | 3.4194 | 3.4911 | 3.5717 | 3.6639 |

| $n$ | $n_1$ | $n_2$ | 0.94 | 0.95 | 0.96 | 0.97 | 0.98 | 0.99 | 0.991 | 0.992 | 0.993 | 0.994 | 0.995 | 0.996 | 0.997 | 0.998 | 0.999 |
|---|---|---|---|---|---|---|---|---|---|---|---|---|---|---|---|---|---|
| 4 | 2 | 2 | 21.21 | 25.452 | 31.838 | 42.504 | 63.794 | 127.48 | 141.63 | 159.25 | 181.76 | 211.88 | 254.65 | 317.97 | 423.53 | 634.62 | 1263.1 |
| 5 | 2 | 3 | 8.0741 | 8.859 | 9.9259 | 11.481 | 14.084 | 19.953 | 21.03 | 22.298 | 23.832 | 25.751 | 28.244 | 31.552 | 36.453 | 44.616 | 63.126 |
| 6 | 3 | 3 | 5.842 | 6.2322 | 6.7397 | 7.4504 | 8.5696 | 10.858 | 11.251 | 11.714 | 12.258 | 12.903 | 13.729 | 14.792 | 16.285 | 18.676 | 23.61 |
| 6 | 2 | 4 | 5.4719 | 5.8411 | 6.3217 | 6.9971 | 8.0562 | 10.225 | 10.596 | 11.03 | 11.544 | 12.163 | 12.933 | 13.94 | 15.375 | 17.613 | 22.255 |
| 7 | 3 | 4 | 4.8134 | 5.0688 | 5.3965 | 5.8409 | 6.5205 | 7.8397 | 8.0599 | 8.3134 | 8.6104 | 8.9638 | 9.3959 | 9.9553 | 10.716 | 11.892 | 14.173 |
| 7 | 2 | 5 | 4.6048 | 4.8519 | 5.1687 | 5.5994 | 6.2566 | 7.5338 | 7.7435 | 7.9859 | 8.2736 | 8.6125 | 9.0308 | 9.5705 | 10.308 | 11.431 | 13.652 |
| 8 | 4 | 4 | 4.3309 | 4.5272 | 4.7742 | 5.1066 | 5.6045 | 6.5401 | 6.6921 | 6.8664 | 7.0679 | 7.3068 | 7.6008 | 7.9701 | 8.4715 | 9.2238 | 10.658 |
| 8 | 3 | 5 | 4.3298 | 4.5252 | 4.7725 | 5.1051 | 5.603 | 6.5385 | 6.6893 | 6.864 | 7.0642 | 7.3035 | 7.5956 | 7.9682 | 8.4738 | 9.2302 | 10.688 |
| 8 | 2 | 6 | 4.189 | 4.3805 | 4.6226 | 4.9479 | 5.4336 | 6.3471 | 6.4959 | 6.6673 | 6.8664 | 7.1029 | 7.3902 | 7.7514 | 8.2382 | 8.9709 | 10.374 |
| 9 | 4 | 5 | 4.057 | 4.2193 | 4.4235 | 4.6945 | 5.0959 | 5.8338 | 5.9521 | 6.0864 | 6.243 | 6.4267 | 6.6491 | 6.931 | 7.3139 | 7.8624 | 8.8933 |
| 9 | 3 | 6 | 4.0584 | 4.2219 | 4.4268 | 4.699 | 5.1007 | 5.8406 | 5.9596 | 6.0949 | 6.2507 | 6.4358 | 6.658 | 6.9407 | 7.3176 | 7.8757 | 8.9198 |
| 9 | 2 | 7 | 3.955 | 4.1161 | 4.3176 | 4.5862 | 4.9827 | 5.7141 | 5.8325 | 5.9665 | 6.1214 | 6.3039 | 6.5236 | 6.7986 | 7.1702 | 7.7184 | 8.7495 |
| 10 | 5 | 5 | 3.8876 | 4.0297 | 4.2076 | 4.4423 | 4.7864 | 5.4097 | 5.5092 | 5.6208 | 5.7491 | 5.901 | 6.0845 | 6.313 | 6.6173 | 7.0672 | 7.8932 |
| 10 | 4 | 6 | 3.8877 | 4.0303 | 4.2085 | 4.4425 | 4.7852 | 5.409 | 5.5074 | 5.6194 | 5.7479 | 5.8984 | 6.08 | 6.3076 | 6.6131 | 7.0614 | 7.8809 |
| 10 | 3 | 7 | 3.8868 | 4.0294 | 4.2074 | 4.4422 | 4.7847 | 5.4062 | 5.5052 | 5.617 | 5.745 | 5.8961 | 6.0776 | 6.302 | 6.6094 | 7.0569 | 7.8773 |
| 10 | 2 | 8 | 3.8044 | 3.9457 | 4.1213 | 4.3535 | 4.6929 | 5.3091 | 5.4074 | 5.5181 | 5.6463 | 5.7958 | 5.9778 | 6.2027 | 6.5024 | 6.9406 | 7.7518 |
| 11 | 5 | 6 | 3.7717 | 3.9 | 4.0593 | 4.2692 | 4.5718 | 5.1151 | 5.2011 | 5.2987 | 5.4102 | 5.5408 | 5.6973 | 5.8938 | 6.1528 | 6.5331 | 7.2131 |
| 11 | 4 | 7 | 3.7713 | 3.8993 | 4.059 | 4.2685 | 4.5734 | 5.1184 | 5.2048 | 5.3003 | 5.4115 | 5.5406 | 5.6973 | 5.8927 | 6.1503 | 6.5254 | 7.2061 |

FIG. 11

Table 3- Method 3 (continued)

| | | | | | | | | | | | | | | | | |
|---|---|---|---|---|---|---|---|---|---|---|---|---|---|---|---|---|
| 11 | 3 | 8 | 2.9513 | 2.9854 | 3.0213 | 3.0593 | 3.0998 | 3.1431 | 3.1894 | 3.2393 | 3.2934 | 3.3522 | 3.4169 | 3.4894 | 3.5704 | 3.663 |
| 11 | 2 | 9 | 2.8966 | 2.9302 | 2.9656 | 3.0031 | 3.0429 | 3.0854 | 3.1311 | 3.1802 | 3.2335 | 3.2918 | 3.3561 | 3.4275 | 3.508 | 3.5997 |
| 12 | 6 | 6 | 2.9312 | 2.9632 | 2.9968 | 3.0324 | 3.0701 | 3.1103 | 3.1532 | 3.1992 | 3.2491 | 3.3036 | 3.3636 | 3.4303 | 3.5052 | 3.5902 |
| 12 | 5 | 7 | 2.931 | 2.963 | 2.9967 | 3.0322 | 3.0699 | 3.1099 | 3.153 | 3.1994 | 3.2496 | 3.3042 | 3.3641 | 3.4304 | 3.5052 | 3.5905 |
| 12 | 4 | 8 | 2.93 | 2.9619 | 2.9956 | 3.0312 | 3.069 | 3.1093 | 3.1523 | 3.1987 | 3.2489 | 3.3038 | 3.3638 | 3.4303 | 3.5052 | 3.5903 |
| 12 | 3 | 9 | 2.9261 | 2.9583 | 2.9921 | 3.0279 | 3.0657 | 3.1061 | 3.1494 | 3.1958 | 3.2462 | 3.3009 | 3.3611 | 3.428 | 3.5032 | 3.589 |
| 12 | 2 | 10 | 2.879 | 2.9106 | 2.944 | 2.9794 | 3.0168 | 3.0567 | 3.0995 | 3.1453 | 3.1951 | 3.2494 | 3.3091 | 3.3755 | 3.45 | 3.535 |
| 13 | 6 | 7 | 2.9143 | 2.9446 | 2.9766 | 3.0102 | 3.0462 | 3.0842 | 3.125 | 3.1687 | 3.216 | 3.2675 | 3.3242 | 3.3867 | 3.4567 | 3.5368 |
| 13 | 5 | 8 | 2.914 | 2.9443 | 2.9764 | 3.0102 | 3.046 | 3.0841 | 3.1249 | 3.1687 | 3.2161 | 3.2677 | 3.3242 | 3.3868 | 3.4569 | 3.5368 |
| 13 | 4 | 9 | 2.9136 | 2.9441 | 2.9762 | 3.01 | 3.0458 | 3.0839 | 3.1247 | 3.1687 | 3.2162 | 3.2679 | 3.3244 | 3.3872 | 3.4577 | 3.5379 |
| 13 | 3 | 10 | 2.9101 | 2.9406 | 2.9727 | 3.0066 | 3.0424 | 3.0807 | 3.1216 | 3.1657 | 3.2131 | 3.2648 | 3.3218 | 3.3848 | 3.4555 | 3.5361 |
| 13 | 2 | 11 | 2.8693 | 2.8994 | 2.9312 | 2.9647 | 3.0003 | 3.0381 | 3.0786 | 3.1222 | 3.1693 | 3.2208 | 3.2772 | 3.3396 | 3.4097 | 3.4892 |
| 14 | 7 | 7 | 2.9033 | 2.9324 | 2.9629 | 2.9953 | 3.0297 | 3.066 | 3.1047 | 3.1465 | 3.1914 | 3.2405 | 3.2941 | 3.3537 | 3.42 | 3.4954 |
| 14 | 6 | 8 | 2.9034 | 2.9326 | 2.9632 | 2.9955 | 3.0297 | 3.0661 | 3.105 | 3.1469 | 3.192 | 3.2411 | 3.2948 | 3.3544 | 3.4211 | 3.4968 |
| 14 | 5 | 9 | 2.9026 | 2.9317 | 2.9623 | 2.9947 | 3.0288 | 3.0651 | 3.1039 | 3.1458 | 3.1908 | 3.2399 | 3.2938 | 3.3535 | 3.4203 | 3.4962 |
| 14 | 4 | 10 | 2.9022 | 2.9314 | 2.9621 | 2.9942 | 3.0286 | 3.0652 | 3.1042 | 3.1459 | 3.1911 | 3.2401 | 3.294 | 3.3539 | 3.4208 | 3.4967 |
| 14 | 3 | 11 | 2.8992 | 2.9283 | 2.9591 | 2.9915 | 3.0258 | 3.0625 | 3.1016 | 3.1435 | 3.1887 | 3.2381 | 3.2919 | 3.3516 | 3.4184 | 3.4942 |
| 14 | 2 | 12 | 2.864 | 2.893 | 2.9233 | 2.9555 | 2.9896 | 3.0258 | 3.0644 | 3.1059 | 3.1509 | 3.1998 | 3.2537 | 3.3132 | 3.3799 | 3.4554 |
| 15 | 7 | 8 | 2.8967 | 2.9246 | 2.9541 | 2.9851 | 3.0181 | 3.0531 | 3.0904 | 3.1305 | 3.1739 | 3.2208 | 3.2723 | 3.3292 | 3.3929 | 3.4656 |
| 15 | 6 | 9 | 2.8969 | 2.9248 | 2.9543 | 2.9855 | 3.0185 | 3.0534 | 3.0908 | 3.1311 | 3.1744 | 3.2212 | 3.2728 | 3.3298 | 3.3934 | 3.4657 |
| 15 | 5 | 10 | 2.8963 | 2.9243 | 2.9538 | 2.9848 | 3.0179 | 3.0528 | 3.0901 | 3.1302 | 3.1736 | 3.2207 | 3.2722 | 3.3293 | 3.393 | 3.4654 |

| | | | | | | | | | | | | | | |
|---|---|---|---|---|---|---|---|---|---|---|---|---|---|---|
| 3.7708 | 3.8997 | 4.0593 | 4.2697 | 4.5745 | 5.1203 | 5.2071 | 5.3039 | 5.4155 | 5.5453 | 5.704 | 5.8965 | 6.1549 | 6.5315 | 7.2213 |
| 3.7063 | 3.8338 | 3.9927 | 4.2009 | 4.5015 | 5.0418 | 5.1266 | 5.2212 | 5.33 | 5.4598 | 5.6142 | 5.8078 | 6.0626 | 6.4356 | 7.1135 |
| 3.689 | 3.8075 | 3.9535 | 4.1459 | 4.4214 | 4.9091 | 4.9857 | 5.0713 | 5.1695 | 5.2862 | 5.4254 | 5.5987 | 5.8244 | 6.1527 | 6.7406 |
| 3.6896 | 3.8079 | 3.9546 | 4.1471 | 4.424 | 4.9146 | 4.9912 | 5.0782 | 5.1781 | 5.2945 | 5.4315 | 5.6034 | 5.8323 | 6.1629 | 6.7581 |
| 3.6894 | 3.8082 | 3.9548 | 4.1471 | 4.424 | 4.9165 | 4.9935 | 5.0803 | 5.1795 | 5.2957 | 5.4356 | 5.6085 | 5.8354 | 6.1643 | 6.757 |
| 3.6883 | 3.8069 | 3.9535 | 4.1453 | 4.4229 | 4.9154 | 4.9921 | 5.0796 | 5.1784 | 5.2945 | 5.433 | 5.605 | 5.8324 | 6.1599 | 6.7614 |
| 3.6334 | 3.7515 | 3.8972 | 4.0869 | 4.3612 | 4.8491 | 4.9251 | 5.0114 | 5.1085 | 5.224 | 5.3596 | 5.5296 | 5.7527 | 6.0811 | 6.6697 |
| 3.6293 | 3.7398 | 3.8763 | 4.0539 | 4.3095 | 4.7597 | 4.8296 | 4.9085 | 4.9985 | 5.1043 | 5.2295 | 5.3878 | 5.593 | 5.89 | 6.4252 |
| 3.6294 | 3.7396 | 3.8761 | 4.0538 | 4.3088 | 4.7583 | 4.8284 | 4.9074 | 4.9979 | 5.103 | 5.229 | 5.3858 | 5.5919 | 5.8864 | 6.4176 |
| 3.6307 | 3.7415 | 3.8775 | 4.0556 | 4.3103 | 4.7618 | 4.8316 | 4.9108 | 5.0003 | 5.1045 | 5.232 | 5.3884 | 5.5908 | 5.8842 | 6.4083 |
| 3.629 | 3.7394 | 3.8762 | 4.0534 | 4.3089 | 4.7604 | 4.8315 | 4.9112 | 5.0007 | 5.1059 | 5.2315 | 5.3851 | 5.5897 | 5.8893 | 6.4217 |
| 3.5818 | 3.6922 | 3.8281 | 4.0056 | 4.2604 | 4.7097 | 4.7794 | 4.8584 | 4.9477 | 5.0527 | 5.1775 | 5.3327 | 5.5365 | 5.8308 | 6.3499 |
| 3.5837 | 3.6878 | 3.8159 | 3.9829 | 4.2218 | 4.6408 | 4.7064 | 4.7783 | 4.8608 | 4.9573 | 5.0723 | 5.2154 | 5.4023 | 5.6733 | 6.1473 |
| 3.5846 | 3.6888 | 3.8177 | 3.984 | 4.2229 | 4.6423 | 4.7074 | 4.7797 | 4.8627 | 4.9599 | 5.076 | 5.2182 | 5.4043 | 5.6742 | 6.1534 |
| 3.5839 | 3.6883 | 3.817 | 3.9844 | 4.2233 | 4.6423 | 4.7074 | 4.7808 | 4.8652 | 4.9624 | 5.0786 | 5.2218 | 5.4086 | 5.6811 | 6.163 |
| 3.5846 | 3.6891 | 3.818 | 3.9856 | 4.2249 | 4.6455 | 4.7107 | 4.7835 | 4.8678 | 4.9647 | 5.0807 | 5.2225 | 5.4119 | 5.6832 | 6.1614 |
| 3.5824 | 3.6867 | 3.8156 | 3.9831 | 4.2221 | 4.6407 | 4.7063 | 4.7799 | 4.8633 | 4.9602 | 5.075 | 5.2174 | 5.404 | 5.6769 | 6.1516 |
| 3.5433 | 3.6475 | 3.7759 | 3.9425 | 4.1803 | 4.597 | 4.6617 | 4.7344 | 4.8186 | 4.9147 | 5.03 | 5.1732 | 5.3589 | 5.6288 | 6.1082 |
| 3.5491 | 3.6484 | 3.771 | 3.9297 | 4.1556 | 4.549 | 4.6096 | 4.6782 | 4.7562 | 4.847 | 4.9539 | 5.0878 | 5.2612 | 5.511 | 5.9515 |
| 3.5493 | 3.6487 | 3.7708 | 3.9297 | 4.1566 | 4.5513 | 4.6126 | 4.6811 | 4.7591 | 4.8501 | 4.959 | 5.0928 | 5.2709 | 5.5195 | 5.9582 |
| 3.5496 | 3.6488 | 3.7704 | 3.929 | 4.1545 | 4.5501 | 4.6106 | 4.6798 | 4.7577 | 4.8491 | 4.9567 | 5.0911 | 5.2638 | 5.5173 | 5.9534 |

FIG. 12

Table 3- Method 3 (continued)

| | | | | | | | | | | | | | | | | |
|---|---|---|---|---|---|---|---|---|---|---|---|---|---|---|---|---|
| 15 | 4 | 11 | 2.8948 | 2.9227 | 2.9523 | 2.9834 | 3.0164 | 3.0515 | 3.089 | 3.1291 | 3.1724 | 3.2196 | 3.271 | 3.3282 | 3.392 | 3.4645 |
| 15 | 3 | 12 | 2.8925 | 2.9205 | 2.9501 | 2.9813 | 3.0144 | 3.0497 | 3.0873 | 3.1276 | 3.171 | 3.2183 | 3.2698 | 3.327 | 3.3909 | 3.4634 |
| 15 | 2 | 13 | 2.8606 | 2.8885 | 2.9179 | 2.949 | 2.9818 | 3.0168 | 3.0542 | 3.0941 | 3.1372 | 3.1841 | 3.2356 | 3.2926 | 3.3563 | 3.4284 |
| 16 | 8 | 8 | 2.8927 | 2.9199 | 2.9486 | 2.9787 | 3.0106 | 3.0444 | 3.0804 | 3.1192 | 3.1611 | 3.2065 | 3.2564 | 3.3114 | 3.3727 | 3.4424 |
| 16 | 7 | 9 | 2.8931 | 2.9202 | 2.9488 | 2.9789 | 3.0107 | 3.0446 | 3.0807 | 3.1195 | 3.1615 | 3.207 | 3.2566 | 3.3112 | 3.3724 | 3.4423 |
| 16 | 6 | 10 | 2.8922 | 2.9195 | 2.9479 | 2.978 | 3.0098 | 3.0437 | 3.0799 | 3.1186 | 3.1603 | 3.2057 | 3.2554 | 3.3103 | 3.3718 | 3.4414 |
| 16 | 5 | 11 | 2.8918 | 2.9192 | 2.9478 | 2.9778 | 3.0098 | 3.0436 | 3.0799 | 3.1188 | 3.1606 | 3.2062 | 3.2558 | 3.3108 | 3.3722 | 3.4419 |
| 16 | 4 | 12 | 2.8916 | 2.9188 | 2.9475 | 2.9776 | 3.0096 | 3.0436 | 3.0799 | 3.1188 | 3.1607 | 3.206 | 3.2559 | 3.3108 | 3.3721 | 3.4419 |
| 16 | 3 | 13 | 2.8892 | 2.9164 | 2.9452 | 2.9754 | 3.0074 | 3.0414 | 3.0776 | 3.1165 | 3.1584 | 3.2039 | 3.2538 | 3.3088 | 3.3705 | 3.4402 |
| 16 | 2 | 14 | 2.8605 | 2.8875 | 2.9159 | 2.9459 | 2.9777 | 3.0115 | 3.0477 | 3.0863 | 3.128 | 3.1732 | 3.223 | 3.2778 | 3.3392 | 3.4085 |
| 17 | 8 | 9 | 2.891 | 2.9174 | 2.9453 | 2.9746 | 3.0056 | 3.0385 | 3.0736 | 3.1111 | 3.1517 | 3.1956 | 3.2438 | 3.2967 | 3.356 | 3.4231 |
| 17 | 7 | 10 | 2.8907 | 2.9172 | 2.945 | 2.9744 | 3.0053 | 3.0382 | 3.0733 | 3.111 | 3.1516 | 3.1954 | 3.2435 | 3.2967 | 3.3561 | 3.4234 |
| 17 | 6 | 11 | 2.8906 | 2.917 | 2.9448 | 2.9741 | 3.0052 | 3.0381 | 3.0732 | 3.1108 | 3.1513 | 3.1953 | 3.2436 | 3.2967 | 3.3559 | 3.4231 |
| 17 | 5 | 12 | 2.8904 | 2.9168 | 2.9446 | 2.9739 | 3.005 | 3.0379 | 3.073 | 3.1107 | 3.1514 | 3.1953 | 3.2435 | 3.2969 | 3.3562 | 3.4237 |
| 17 | 4 | 13 | 2.8898 | 2.9164 | 2.9442 | 2.9735 | 3.0043 | 3.0372 | 3.0724 | 3.1102 | 3.1508 | 3.1947 | 3.2429 | 3.2961 | 3.3555 | 3.423 |
| 17 | 3 | 14 | 2.8874 | 2.9139 | 2.9418 | 2.9712 | 3.0021 | 3.0351 | 3.0702 | 3.1079 | 3.1484 | 3.1927 | 3.2408 | 3.294 | 3.3536 | 3.421 |
| 17 | 2 | 15 | 2.8616 | 2.888 | 2.9157 | 2.945 | 2.9759 | 3.0088 | 3.0439 | 3.0814 | 3.122 | 3.166 | 3.2138 | 3.2668 | 3.326 | 3.3931 |
| 18 | 9 | 9 | 2.8904 | 2.9162 | 2.9434 | 2.972 | 3.0022 | 3.0342 | 3.0685 | 3.105 | 3.1444 | 3.1871 | 3.2338 | 3.2856 | 3.3432 | 3.4085 |
| 18 | 8 | 10 | 2.8907 | 2.9165 | 2.9437 | 2.9723 | 3.0025 | 3.0346 | 3.0687 | 3.1053 | 3.1448 | 3.1876 | 3.2344 | 3.286 | 3.3435 | 3.4089 |
| 18 | 7 | 11 | 2.8903 | 2.9161 | 2.9431 | 2.9717 | 3.0019 | 3.034 | 3.0683 | 3.1048 | 3.1443 | 3.187 | 3.2338 | 3.2854 | 3.343 | 3.4082 |
| 18 | 6 | 12 | 2.8905 | 2.9162 | 2.9433 | 2.9719 | 3.0021 | 3.0343 | 3.0686 | 3.1052 | 3.1445 | 3.1872 | 3.2339 | 3.2853 | 3.343 | 3.4083 |

| | | | | | | | | | | | | | | |
|---|---|---|---|---|---|---|---|---|---|---|---|---|---|---|
| 3.5489 | 3.6486 | 3.7709 | 3.9295 | 4.1555 | 4.5491 | 4.6099 | 4.6789 | 4.7575 | 4.8475 | 4.9554 | 5.0909 | 5.264 | 5.515 | 5.9568 |
| 3.5475 | 3.6471 | 3.7697 | 3.9281 | 4.1545 | 4.55 | 4.6109 | 4.6793 | 4.7568 | 4.8482 | 4.9554 | 5.0889 | 5.2631 | 5.5135 | 5.9555 |
| 3.5121 | 3.6112 | 3.7336 | 3.8918 | 4.1172 | 4.5105 | 4.5711 | 4.6388 | 4.717 | 4.8072 | 4.9161 | 5.0496 | 5.2235 | 5.4744 | 5.9135 |
| 3.5226 | 3.6178 | 3.7349 | 3.8865 | 4.1015 | 4.4758 | 4.5335 | 4.5986 | 4.6715 | 4.7572 | 4.8592 | 4.9861 | 5.1495 | 5.3817 | 5.7944 |
| 3.5228 | 3.618 | 3.7355 | 3.8867 | 4.102 | 4.4768 | 4.5342 | 4.599 | 4.672 | 4.7575 | 4.8595 | 4.9846 | 5.1484 | 5.3838 | 5.7939 |
| 3.5216 | 3.6169 | 3.7338 | 3.8858 | 4.1015 | 4.4754 | 4.5332 | 4.5973 | 4.6716 | 4.757 | 4.8607 | 4.9864 | 5.1518 | 5.3853 | 5.793 |
| 3.5223 | 3.6177 | 3.7345 | 3.8856 | 4.1008 | 4.474 | 4.532 | 4.5969 | 4.6702 | 4.755 | 4.8562 | 4.98 | 5.1444 | 5.3787 | 5.7901 |
| 3.523 | 3.6185 | 3.7352 | 3.8865 | 4.1018 | 4.4768 | 4.5341 | 4.5991 | 4.6733 | 4.76 | 4.8619 | 4.9879 | 5.1511 | 5.3831 | 5.7946 |
| 3.5207 | 3.6165 | 3.7337 | 3.8855 | 4.1008 | 4.4746 | 4.5324 | 4.5971 | 4.6709 | 4.7565 | 4.8577 | 4.9837 | 5.1475 | 5.3832 | 5.7954 |
| 3.4888 | 3.5839 | 3.7009 | 3.8516 | 4.0665 | 4.4401 | 4.4977 | 4.5621 | 4.6356 | 4.7211 | 4.8218 | 4.9466 | 5.1085 | 5.3413 | 5.7515 |
| 3.5007 | 3.5923 | 3.7047 | 3.8502 | 4.057 | 4.4146 | 4.47 | 4.5319 | 4.6018 | 4.6819 | 4.7796 | 4.899 | 5.0549 | 5.275 | 5.6592 |
| 3.5009 | 3.5924 | 3.7053 | 3.8509 | 4.0565 | 4.4147 | 4.4691 | 4.5308 | 4.6008 | 4.6814 | 4.7771 | 4.8962 | 5.0513 | 5.2756 | 5.6651 |
| 3.5008 | 3.5927 | 3.7049 | 3.8501 | 4.0568 | 4.4145 | 4.4694 | 4.5315 | 4.6016 | 4.6827 | 4.7801 | 4.8985 | 5.0548 | 5.276 | 5.6665 |
| 3.5013 | 3.5935 | 3.7059 | 3.8516 | 4.0585 | 4.4168 | 4.4721 | 4.533 | 4.6031 | 4.6843 | 4.781 | 4.8985 | 5.0555 | 5.2744 | 5.6667 |
| 3.5006 | 3.5921 | 3.705 | 3.8507 | 4.0571 | 4.4142 | 4.4693 | 4.5313 | 4.601 | 4.6818 | 4.7779 | 4.8969 | 5.0525 | 5.2731 | 5.6554 |
| 3.4991 | 3.5913 | 3.7039 | 3.8497 | 4.0567 | 4.4133 | 4.4676 | 4.5282 | 4.5979 | 4.679 | 4.7756 | 4.8956 | 5.0504 | 5.2702 | 5.6541 |
| 3.4704 | 3.5622 | 3.6744 | 3.8202 | 4.0261 | 4.3821 | 4.4367 | 4.4976 | 4.5677 | 4.648 | 4.7449 | 4.863 | 5.018 | 5.237 | 5.6207 |
| 3.4837 | 3.5727 | 3.6817 | 3.8213 | 4.0202 | 4.3629 | 4.4153 | 4.4751 | 4.5421 | 4.6195 | 4.7106 | 4.8239 | 4.9712 | 5.1799 | 5.5444 |
| 3.484 | 3.5725 | 3.6811 | 3.8217 | 4.0205 | 4.3639 | 4.4163 | 4.4751 | 4.5428 | 4.621 | 4.7135 | 4.8281 | 4.9754 | 5.1844 | 5.5473 |
| 3.4834 | 3.572 | 3.6811 | 3.8212 | 4.0208 | 4.3641 | 4.4164 | 4.4752 | 4.5417 | 4.6194 | 4.7115 | 4.8254 | 4.9737 | 5.1862 | 5.5484 |
| 3.4838 | 3.5724 | 3.6814 | 3.8222 | 4.021 | 4.3646 | 4.4172 | 4.4765 | 4.5433 | 4.6211 | 4.7125 | 4.8272 | 4.9757 | 5.1878 | 5.5519 |

FIG. 13

Table 3- Method 3 (continued)

| | | | | | | | | | | | | | | | | |
|---|---|---|---|---|---|---|---|---|---|---|---|---|---|---|---|---|
| 18 | 5 | 13 | 2.8902 | 2.916 | 2.9431 | 2.9716 | 3.0018 | 3.0339 | 3.0681 | 3.1048 | 3.1444 | 3.1872 | 3.2338 | 3.2854 | 3.3427 | 3.408 |
| 18 | 4 | 14 | 2.8894 | 2.9151 | 2.9423 | 2.9709 | 3.0011 | 3.0332 | 3.0674 | 3.1042 | 3.1438 | 3.1865 | 3.2332 | 3.2848 | 3.3426 | 3.4079 |
| 18 | 3 | 15 | 2.8876 | 2.9135 | 2.9405 | 2.9691 | 2.9994 | 3.0316 | 3.0658 | 3.1025 | 3.142 | 3.1847 | 3.2315 | 3.2834 | 3.3409 | 3.4064 |
| 18 | 2 | 16 | 2.8633 | 2.8891 | 2.9161 | 2.9446 | 2.9747 | 3.0068 | 3.0409 | 3.0773 | 3.1167 | 3.1592 | 3.206 | 3.2575 | 3.3152 | 3.3806 |
| 19 | 9 | 10 | 2.8913 | 2.9165 | 2.943 | 2.971 | 3.0005 | 3.0319 | 3.0653 | 3.1011 | 3.1395 | 3.1812 | 3.2269 | 3.2772 | 3.3334 | 3.3968 |
| 19 | 8 | 11 | 2.8914 | 2.9167 | 2.9432 | 2.9712 | 3.0007 | 3.032 | 3.0654 | 3.1011 | 3.1395 | 3.1812 | 3.2267 | 3.277 | 3.3331 | 3.3964 |
| 19 | 7 | 12 | 2.8911 | 2.9164 | 2.9429 | 2.9709 | 3.0005 | 3.0318 | 3.0652 | 3.1009 | 3.1393 | 3.1811 | 3.2266 | 3.2769 | 3.333 | 3.3964 |
| 19 | 6 | 13 | 2.8912 | 2.9166 | 2.9431 | 2.9711 | 3.0005 | 3.0319 | 3.0653 | 3.1011 | 3.1396 | 3.1813 | 3.227 | 3.2774 | 3.3335 | 3.3969 |
| 19 | 5 | 14 | 2.8906 | 2.9159 | 2.9425 | 2.9704 | 3 | 3.0314 | 3.0648 | 3.1005 | 3.1391 | 3.1808 | 3.2265 | 3.277 | 3.3331 | 3.3965 |
| 19 | 4 | 15 | 2.89 | 2.9152 | 2.9417 | 2.9697 | 2.9993 | 3.0306 | 3.0639 | 3.0996 | 3.1382 | 3.18 | 3.2261 | 3.2764 | 3.3325 | 3.3959 |
| 19 | 3 | 16 | 2.8885 | 2.9139 | 2.9405 | 2.9685 | 2.9981 | 3.0296 | 3.0631 | 3.0989 | 3.1375 | 3.1794 | 3.2252 | 3.2755 | 3.3318 | 3.3951 |
| 19 | 2 | 17 | 2.8666 | 2.8919 | 2.9183 | 2.9462 | 2.9757 | 3.0068 | 3.0401 | 3.0758 | 3.1143 | 3.1561 | 3.2015 | 3.2518 | 3.3078 | 3.371 |
| 20 | 10 | 10 | 2.8933 | 2.9182 | 2.9443 | 2.9717 | 3.0007 | 3.0313 | 3.0639 | 3.0989 | 3.1366 | 3.1773 | 3.222 | 3.2711 | 3.3257 | 3.3875 |
| 20 | 9 | 11 | 2.8931 | 2.9179 | 2.944 | 2.9714 | 3.0003 | 3.031 | 3.0637 | 3.0987 | 3.1363 | 3.1769 | 3.2215 | 3.2706 | 3.3256 | 3.3874 |
| 20 | 8 | 12 | 2.8931 | 2.918 | 2.9439 | 2.9713 | 3.0003 | 3.031 | 3.0637 | 3.0986 | 3.1361 | 3.1769 | 3.2215 | 3.2705 | 3.3253 | 3.3871 |
| 20 | 7 | 13 | 2.8925 | 2.9172 | 2.9433 | 2.9707 | 2.9995 | 3.0303 | 3.0631 | 3.098 | 3.1357 | 3.1764 | 3.221 | 3.2699 | 3.3245 | 3.3863 |
| 20 | 6 | 14 | 2.8927 | 2.9174 | 2.9435 | 2.9709 | 2.9999 | 3.0306 | 3.0633 | 3.0983 | 3.136 | 3.1767 | 3.221 | 3.2702 | 3.3251 | 3.3871 |
| 20 | 5 | 15 | 2.8927 | 2.9175 | 2.9435 | 2.9708 | 2.9997 | 3.0303 | 3.0631 | 3.098 | 3.1359 | 3.1767 | 3.2214 | 3.2705 | 3.3253 | 3.3873 |
| 20 | 4 | 16 | 2.8922 | 2.9171 | 2.9432 | 2.9705 | 2.9994 | 3.0302 | 3.0629 | 3.0979 | 3.1357 | 3.1766 | 3.2212 | 3.2704 | 3.3252 | 3.3873 |
| 20 | 3 | 17 | 2.8905 | 2.9154 | 2.9415 | 2.9689 | 2.998 | 3.0287 | 3.0614 | 3.0964 | 3.1341 | 3.1752 | 3.2199 | 3.2691 | 3.3242 | 3.3862 |
| 20 | 2 | 18 | 2.8699 | 2.8946 | 2.9207 | 2.9481 | 2.977 | 3.0077 | 3.0403 | 3.0754 | 3.113 | 3.1538 | 3.1983 | 3.2473 | 3.302 | 3.3639 |

| | | | | | | | | | | | | | | | | | |
|---|---|---|---|---|---|---|---|---|---|---|---|---|---|---|---|---|---|
| 18 | 5 | 13 | 3.4833 | 3.5722 | 3.681 | 3.8217 | 4.0203 | 4.3625 | 4.4151 | 4.4737 | 4.5414 | 4.6188 | 4.7112 | 4.8246 | 4.9741 | 5.1838 | 5.5476 |
| 18 | 4 | 14 | 3.4835 | 3.5725 | 3.6813 | 3.8217 | 4.0205 | 4.3638 | 4.4165 | 4.4759 | 4.5424 | 4.6203 | 4.7129 | 4.8273 | 4.9739 | 5.1843 | 5.5505 |
| 18 | 3 | 15 | 3.4817 | 3.571 | 3.6796 | 3.8209 | 4.0203 | 4.3641 | 4.4157 | 4.474 | 4.5414 | 4.6193 | 4.7117 | 4.8249 | 4.9721 | 5.1812 | 5.5494 |
| 18 | 2 | 16 | 3.4559 | 3.5449 | 3.6535 | 3.7941 | 3.9923 | 4.3373 | 4.3903 | 4.4486 | 4.5157 | 4.5934 | 4.6865 | 4.8016 | 4.9496 | 5.1591 | 5.5229 |
| 19 | 9 | 10 | 3.47 | 3.5564 | 3.6621 | 3.7987 | 3.9913 | 4.3233 | 4.3743 | 4.4309 | 4.4961 | 4.5704 | 4.6591 | 4.7692 | 4.91 | 5.1131 | 5.4643 |
| 19 | 8 | 11 | 3.4695 | 3.556 | 3.6618 | 3.7983 | 3.9907 | 4.3222 | 4.3724 | 4.4293 | 4.4938 | 4.5683 | 4.657 | 4.7656 | 4.9092 | 5.1111 | 5.4603 |
| 19 | 7 | 12 | 3.4696 | 3.5559 | 3.6617 | 3.7984 | 3.9905 | 4.3206 | 4.3713 | 4.4279 | 4.4925 | 4.5665 | 4.6539 | 4.7632 | 4.9057 | 5.1081 | 5.4567 |
| 19 | 6 | 13 | 3.47 | 3.5561 | 3.6618 | 3.7981 | 3.9904 | 4.3205 | 4.3717 | 4.4281 | 4.493 | 4.567 | 4.6561 | 4.7648 | 4.905 | 5.1062 | 5.4574 |
| 19 | 5 | 14 | 3.4696 | 3.556 | 3.6615 | 3.7982 | 3.9904 | 4.3213 | 4.3717 | 4.4288 | 4.4933 | 4.568 | 4.658 | 4.7674 | 4.9082 | 5.1094 | 5.4598 |
| 19 | 4 | 15 | 3.4691 | 3.5559 | 3.6616 | 3.7979 | 3.9901 | 4.3214 | 4.372 | 4.4285 | 4.4926 | 4.5669 | 4.6557 | 4.7629 | 4.9039 | 5.1069 | 5.4539 |
| 19 | 3 | 16 | 3.4688 | 3.5551 | 3.6611 | 3.7968 | 3.9892 | 4.3207 | 4.3721 | 4.4286 | 4.4938 | 4.5674 | 4.6559 | 4.7651 | 4.905 | 5.1046 | 5.4492 |
| 19 | 2 | 17 | 3.4442 | 3.5306 | 3.6359 | 3.7718 | 3.964 | 4.2963 | 4.3472 | 4.4044 | 4.4688 | 4.543 | 4.6321 | 4.7399 | 4.8816 | 5.0819 | 5.4308 |
| 20 | 10 | 10 | 3.4589 | 3.5432 | 3.6462 | 3.7788 | 3.9658 | 4.2868 | 4.3359 | 4.3906 | 4.453 | 4.5246 | 4.6099 | 4.7159 | 4.8549 | 5.0492 | 5.383 |
| 20 | 9 | 11 | 3.4589 | 3.5432 | 3.6461 | 3.7787 | 3.9653 | 4.2865 | 4.3356 | 4.3904 | 4.4524 | 4.5243 | 4.6091 | 4.7157 | 4.8537 | 5.0462 | 5.3808 |
| 20 | 8 | 12 | 3.458 | 3.5419 | 3.6448 | 3.7777 | 3.9647 | 4.2866 | 4.3357 | 4.3907 | 4.4536 | 4.5252 | 4.6113 | 4.7161 | 4.8543 | 5.046 | 5.3813 |
| 20 | 7 | 13 | 3.4574 | 3.5414 | 3.644 | 3.7768 | 3.9632 | 4.2835 | 4.3328 | 4.3874 | 4.4491 | 4.5202 | 4.6059 | 4.7105 | 4.8465 | 5.0377 | 5.3744 |
| 20 | 6 | 14 | 3.4585 | 3.5425 | 3.6458 | 3.778 | 3.9653 | 4.2871 | 4.3364 | 4.3909 | 4.4535 | 4.5253 | 4.6115 | 4.7161 | 4.8527 | 5.0458 | 5.3847 |
| 20 | 5 | 15 | 3.4583 | 3.5426 | 3.6457 | 3.7787 | 3.9654 | 4.2871 | 4.336 | 4.3911 | 4.4537 | 4.5258 | 4.6106 | 4.7157 | 4.8521 | 5.0444 | 5.3805 |
| 20 | 4 | 16 | 3.4587 | 3.543 | 3.6461 | 3.7788 | 3.9663 | 4.2884 | 4.3375 | 4.3931 | 4.4555 | 4.5272 | 4.6138 | 4.7187 | 4.8552 | 5.0489 | 5.3862 |
| 20 | 3 | 17 | 3.4577 | 3.5423 | 3.6452 | 3.7779 | 3.9649 | 4.2861 | 4.3349 | 4.389 | 4.4506 | 4.5223 | 4.6075 | 4.7123 | 4.8487 | 5.0412 | 5.3728 |
| 20 | 2 | 18 | 3.4352 | 3.5196 | 3.6226 | 3.7556 | 3.9423 | 4.2625 | 4.3116 | 4.3668 | 4.4286 | 4.5003 | 4.5859 | 4.6903 | 4.8263 | 5.0223 | 5.3528 |

FIG. 14

Table 1 - Method 1 in dimension 2

| n \ level | 0.8 | 0.81 | 0.82 | 0.83 | 0.84 | 0.85 | 0.86 | 0.87 | 0.88 | 0.89 | 0.9 | 0.91 | 0.92 | 0.93 |
|---|---|---|---|---|---|---|---|---|---|---|---|---|---|---|
| 4 | 178.73 | 199.26 | 223.35 | 251.9 | 286.02 | 327.32 | 378.05 | 440.89 | 520.35 | 622.63 | 758.32 | 942.07 | 1200.3 | 1577.3 |
| 5 | 22.859 | 24.177 | 25.644 | 27.284 | 29.124 | 31.209 | 33.591 | 36.337 | 39.53 | 43.321 | 47.856 | 53.414 | 60.346 | 69.271 |
| 6 | 12.576 | 13.087 | 13.647 | 14.26 | 14.94 | 15.691 | 16.53 | 17.472 | 18.54 | 19.763 | 21.185 | 22.869 | 24.9 | 27.392 |
| 7 | 9.5861 | 9.9004 | 10.24 | 10.61 | 11.013 | 11.456 | 11.942 | 12.484 | 13.089 | 13.78 | 14.564 | 15.476 | 16.55 | 17.85 |
| 8 | 8.257 | 8.4907 | 8.7412 | 9.0106 | 9.3036 | 9.6243 | 9.9748 | 10.36 | 10.787 | 11.269 | 11.815 | 12.443 | 13.177 | 14.053 |
| 9 | 7.5286 | 7.7187 | 7.9225 | 8.1416 | 8.378 | 8.6335 | 8.9125 | 9.2204 | 9.5586 | 9.938 | 10.365 | 10.851 | 11.417 | 12.083 |
| 10 | 7.082 | 7.2454 | 7.4199 | 7.6079 | 7.8091 | 8.0266 | 8.2637 | 8.5225 | 8.808 | 9.1244 | 9.4784 | 9.8844 | 10.351 | 10.898 |
| 11 | 6.7852 | 6.931 | 7.0863 | 7.2521 | 7.4302 | 7.6228 | 7.832 | 8.0599 | 8.3101 | 8.5878 | 8.8979 | 9.25 | 9.6522 | 10.122 |
| 12 | 6.5777 | 6.7111 | 6.8531 | 7.0043 | 7.1659 | 7.3405 | 7.5302 | 7.7357 | 7.9624 | 8.2114 | 8.4887 | 8.8027 | 9.1618 | 9.5797 |
| 13 | 6.4311 | 6.5542 | 6.6854 | 6.8253 | 6.9745 | 7.1358 | 7.3099 | 7.4978 | 7.7046 | 7.9333 | 8.1878 | 8.4739 | 8.7998 | 9.1791 |
| 14 | 6.3193 | 6.4353 | 6.5584 | 6.6897 | 6.8298 | 6.9809 | 7.1432 | 7.3203 | 7.5138 | 7.7264 | 7.9617 | 8.2265 | 8.5281 | 8.879 |
| 15 | 6.238 | 6.3482 | 6.4655 | 6.5899 | 6.7223 | 6.8653 | 7.0187 | 7.1853 | 7.3676 | 7.5666 | 7.7899 | 8.0385 | 8.3215 | 8.6493 |
| 16 | 6.1738 | 6.2792 | 6.3909 | 6.5099 | 6.6364 | 6.7721 | 6.9181 | 7.0764 | 7.2495 | 7.4399 | 7.651 | 7.8865 | 8.1545 | 8.4636 |
| 17 | 6.1238 | 6.225 | 6.3324 | 6.4464 | 6.5685 | 6.6989 | 6.8397 | 6.9923 | 7.1578 | 7.3397 | 7.5407 | 7.7659 | 8.0214 | 8.3148 |
| 18 | 6.0874 | 6.1856 | 6.2896 | 6.3998 | 6.5175 | 6.6429 | 6.7784 | 6.9245 | 7.0841 | 7.2584 | 7.4515 | 7.6675 | 7.9119 | 8.1936 |
| 19 | 6.0579 | 6.153 | 6.2535 | 6.3604 | 6.4744 | 6.5962 | 6.727 | 6.8686 | 7.0222 | 7.1907 | 7.3765 | 7.5849 | 7.8205 | 8.0903 |
| 20 | 6.0371 | 6.1299 | 6.2281 | 6.3321 | 6.4424 | 6.5609 | 6.6882 | 6.826 | 6.9753 | 7.1393 | 7.3203 | 7.5218 | 7.749 | 8.0101 |

| 0.94 | 0.95 | 0.96 | 0.97 | 0.98 | 0.99 | 0.991 | 0.992 | 0.993 | 0.994 | 0.995 | 0.996 | 0.997 | 0.998 | 0.999 |
|---|---|---|---|---|---|---|---|---|---|---|---|---|---|---|
| 2158.1 | 3126.9 | 4902.7 | 8740.3 | 19809 | 79591 | 98256 | 1.24E+05 | 1.63E+05 | 2.21E+05 | 3.18E+05 | 4.98E+05 | 8.85E+05 | 2.00E+06 | 8.01E+06 |
| 81.137 | 97.7 | 122.62 | 164.27 | 247.25 | 495.05 | 549.76 | 617.71 | 705.8 | 823.25 | 988.16 | 1234.6 | 1643.4 | 2466.1 | 4953.6 |
| 30.556 | 34.754 | 40.624 | 49.569 | 65.452 | 105.09 | 112.91 | 122.3 | 133.71 | 148.31 | 167.66 | 194.67 | 236.16 | 309.77 | 493.93 |
| 19.467 | 21.543 | 24.349 | 28.452 | 35.305 | 50.846 | 53.742 | 57.141 | 61.276 | 66.368 | 72.93 | 81.772 | 94.664 | 116.57 | 166.32 |
| 15.118 | 16.467 | 18.253 | 20.802 | 24.917 | 33.702 | 35.247 | 37.069 | 39.228 | 41.897 | 45.234 | 49.711 | 56.175 | 66.501 | 88.612 |
| 12.888 | 13.896 | 15.21 | 17.052 | 19.966 | 25.977 | 27.009 | 28.217 | 29.636 | 31.36 | 33.492 | 36.3 | 40.25 | 46.474 | 59.315 |
| 11.554 | 12.369 | 13.422 | 14.876 | 17.147 | 21.667 | 22.44 | 23.327 | 24.377 | 25.633 | 27.175 | 29.193 | 32.02 | 36.342 | 45.217 |
| 10.685 | 11.378 | 12.266 | 13.49 | 15.369 | 19.042 | 19.655 | 20.361 | 21.192 | 22.184 | 23.419 | 24.987 | 27.181 | 30.515 | 37.016 |
| 10.076 | 10.684 | 11.46 | 12.52 | 14.126 | 17.246 | 17.767 | 18.351 | 19.04 | 19.865 | 20.875 | 22.169 | 23.925 | 26.635 | 31.766 |
| 9.6288 | 10.178 | 10.876 | 11.82 | 13.245 | 15.96 | 16.408 | 16.924 | 17.52 | 18.219 | 19.086 | 20.188 | 21.697 | 23.976 | 28.285 |
| 9.2935 | 9.7962 | 10.437 | 11.297 | 12.588 | 15.022 | 15.422 | 15.878 | 16.401 | 17.024 | 17.787 | 18.753 | 20.051 | 21.99 | 25.639 |
| 9.0333 | 9.5023 | 10.095 | 10.89 | 12.081 | 14.295 | 14.654 | 15.062 | 15.537 | 16.101 | 16.783 | 17.645 | 18.809 | 20.554 | 23.802 |
| 8.8273 | 9.2691 | 9.8253 | 10.569 | 11.671 | 13.708 | 14.036 | 14.411 | 14.85 | 15.37 | 15.997 | 16.788 | 17.85 | 19.41 | 22.339 |
| 8.66 | 9.0786 | 9.6041 | 10.305 | 11.345 | 13.267 | 13.577 | 13.927 | 14.334 | 14.811 | 15.387 | 16.112 | 17.081 | 18.523 | 21.174 |
| 8.5235 | 8.9228 | 9.4211 | 10.088 | 11.069 | 12.874 | 13.159 | 13.481 | 13.856 | 14.298 | 14.831 | 15.506 | 16.404 | 17.735 | 20.191 |
| 8.4059 | 8.7888 | 9.2674 | 9.9057 | 10.842 | 12.549 | 12.822 | 13.134 | 13.484 | 13.906 | 14.412 | 15.05 | 15.9 | 17.138 | 19.392 |
| 8.3155 | 8.6832 | 9.1435 | 9.7558 | 10.65 | 12.284 | 12.543 | 12.836 | 13.172 | 13.562 | 14.042 | 14.631 | 15.425 | 16.579 | 18.734 |

FIG. 15

Table 1 - Method 3 in dimension 3

| n \ level | 0.8 | 0.81 | 0.82 | 0.83 | 0.84 | 0.85 | 0.86 | 0.87 | 0.88 | 0.89 | 0.9 | 0.91 | 0.92 | 0.93 |
|---|---|---|---|---|---|---|---|---|---|---|---|---|---|---|
| 5 | 293.01 | 327.18 | 367.23 | 414.81 | 471.68 | 540.7 | 625.29 | 730.43 | 863.8 | 1035.4 | 1261.8 | 1566.7 | 1997.5 | 2623.1 |
| 6 | 27.32 | 28.905 | 30.663 | 32.623 | 34.832 | 37.341 | 40.203 | 43.499 | 47.345 | 51.888 | 57.34 | 64.032 | 72.374 | 83.073 |
| 7 | 13.428 | 13.969 | 14.559 | 15.208 | 15.921 | 16.71 | 17.593 | 18.583 | 19.713 | 21.009 | 22.506 | 24.286 | 26.432 | 29.061 |
| 8 | 9.6607 | 9.971 | 10.307 | 10.67 | 11.067 | 11.502 | 11.981 | 12.515 | 13.113 | 13.788 | 14.564 | 15.46 | 16.521 | 17.8 |
| 9 | 8.01 | 8.2293 | 8.4646 | 8.7183 | 8.9936 | 9.2929 | 9.622 | 9.9858 | 10.389 | 10.841 | 11.353 | 11.942 | 12.628 | 13.444 |
| 10 | 7.1152 | 7.2879 | 7.4729 | 7.6711 | 7.8852 | 8.1178 | 8.3706 | 8.6487 | 8.9546 | 9.2954 | 9.6819 | 10.122 | 10.63 | 11.229 |
| 11 | 6.5574 | 6.7019 | 6.8561 | 7.0213 | 7.1993 | 7.3912 | 7.5995 | 7.8276 | 8.0788 | 8.3596 | 8.6735 | 9.0291 | 9.436 | 9.9155 |
| 12 | 6.1915 | 6.3182 | 6.4529 | 6.5966 | 6.751 | 6.9171 | 7.0973 | 7.2944 | 7.51 | 7.7488 | 8.0158 | 8.3179 | 8.664 | 9.0692 |
| 13 | 5.9317 | 6.0451 | 6.1657 | 6.295 | 6.4327 | 6.5817 | 6.7429 | 6.9176 | 7.1095 | 7.3205 | 7.5558 | 7.8225 | 8.126 | 8.4803 |
| 14 | 5.7388 | 5.8424 | 5.9532 | 6.0712 | 6.1968 | 6.3323 | 6.4785 | 6.6363 | 6.8098 | 7.0007 | 7.2134 | 7.4525 | 7.7238 | 8.04 |
| 15 | 5.5928 | 5.6893 | 5.792 | 5.901 | 6.0175 | 6.1428 | 6.278 | 6.4251 | 6.5848 | 6.7599 | 6.9551 | 7.174 | 7.4227 | 7.7109 |
| 16 | 5.4808 | 5.5716 | 5.6682 | 5.7706 | 5.8803 | 5.9977 | 6.1236 | 6.2603 | 6.4104 | 6.5741 | 6.7553 | 6.9586 | 7.1902 | 7.4568 |
| 17 | 5.3913 | 5.4774 | 5.5686 | 5.6657 | 5.7692 | 5.8797 | 5.9991 | 6.128 | 6.2686 | 6.4228 | 6.5939 | 6.7846 | 7.0016 | 7.2515 |
| 18 | 5.319 | 5.4013 | 5.4879 | 5.5804 | 5.6789 | 5.7841 | 5.8977 | 6.0202 | 6.1538 | 6.2996 | 6.4615 | 6.6415 | 6.8471 | 7.0828 |
| 19 | 5.2603 | 5.3396 | 5.423 | 5.5118 | 5.606 | 5.7074 | 5.816 | 5.9331 | 6.0606 | 6.2006 | 6.3545 | 6.5273 | 6.7224 | 6.9461 |
| 20 | 5.2129 | 5.2891 | 5.3697 | 5.4552 | 5.5462 | 5.6436 | 5.7479 | 5.8606 | 5.9832 | 6.117 | 6.2642 | 6.429 | 6.6161 | 6.8308 |

| n \ level | 0.94 | 0.95 | 0.96 | 0.97 | 0.98 | 0.99 | 0.991 | 0.992 | 0.993 | 0.994 | 0.995 | 0.996 | 0.997 | 0.998 | 0.999 |
|---|---|---|---|---|---|---|---|---|---|---|---|---|---|---|---|
| 5 | 3593.1 | 5214.4 | 8210.2 | 14699 | 33278 | 1.35E+05 | 1.67E+05 | 2.11E+05 | 2.76E+05 | 3.77E+05 | 5.44E+05 | 8.50E+05 | 1.51E+06 | 3.41E+06 | 1.36E+07 |
| 6 | 97.309 | 117.3 | 147.22 | 197.15 | 296.72 | 597.3 | 663.21 | 746.27 | 852.81 | 996.79 | 1196.7 | 1498.9 | 1999.8 | 3002.9 | 6011.6 |
| 7 | 32.402 | 36.818 | 42.998 | 52.426 | 69.221 | 110.63 | 118.85 | 128.84 | 140.98 | 156.32 | 177.09 | 205.65 | 249.49 | 327.02 | 517.24 |
| 8 | 19.373 | 21.408 | 24.148 | 28.167 | 34.884 | 50.1 | 52.907 | 56.26 | 60.281 | 65.215 | 71.581 | 80.268 | 92.876 | 114.04 | 161.51 |
| 9 | 14.437 | 15.696 | 17.366 | 19.728 | 23.558 | 31.756 | 33.218 | 34.944 | 36.953 | 39.459 | 42.591 | 46.765 | 52.695 | 62.275 | 83.032 |
| 10 | 11.957 | 12.861 | 14.043 | 15.701 | 18.315 | 23.683 | 24.613 | 25.69 | 26.975 | 28.523 | 30.444 | 32.979 | 36.526 | 42.106 | 53.637 |
| 11 | 10.49 | 11.201 | 12.129 | 13.401 | 15.386 | 19.344 | 20.017 | 20.803 | 21.717 | 22.82 | 24.176 | 25.913 | 28.382 | 32.138 | 39.725 |
| 12 | 9.5508 | 10.145 | 10.905 | 11.948 | 13.55 | 16.688 | 17.217 | 17.828 | 18.54 | 19.396 | 20.441 | 21.777 | 23.587 | 26.407 | 31.972 |
| 13 | 8.8991 | 9.4122 | 10.066 | 10.956 | 12.311 | 14.925 | 15.362 | 15.856 | 16.437 | 17.126 | 17.963 | 19.064 | 20.535 | 22.777 | 27.061 |
| 14 | 8.4151 | 8.87 | 9.4505 | 10.234 | 11.417 | 13.674 | 14.043 | 14.465 | 14.956 | 15.531 | 16.238 | 17.149 | 18.389 | 20.262 | 23.852 |
| 15 | 8.0501 | 8.4639 | 8.9889 | 9.695 | 10.752 | 12.74 | 13.066 | 13.436 | 13.859 | 14.372 | 14.989 | 15.776 | 16.851 | 18.446 | 21.499 |
| 16 | 7.7703 | 8.1528 | 8.6334 | 9.2783 | 10.24 | 12.043 | 12.332 | 12.666 | 13.05 | 13.5 | 14.058 | 14.755 | 15.689 | 17.075 | 19.718 |
| 17 | 7.544 | 7.8992 | 8.3462 | 8.9445 | 9.8302 | 11.479 | 11.743 | 12.043 | 12.39 | 12.797 | 13.293 | 13.921 | 14.76 | 15.995 | 18.323 |
| 18 | 7.3605 | 7.6944 | 8.1136 | 8.6736 | 9.5014 | 11.016 | 11.259 | 11.533 | 11.853 | 12.225 | 12.681 | 13.256 | 14.033 | 15.184 | 17.308 |
| 19 | 7.208 | 7.5242 | 7.9223 | 8.4508 | 9.2265 | 10.651 | 10.879 | 11.138 | 11.434 | 11.785 | 12.212 | 12.744 | 13.448 | 14.489 | 16.406 |
| 20 | 7.0812 | 7.3831 | 7.7602 | 8.2618 | 8.9975 | 10.338 | 10.552 | 10.792 | 11.071 | 11.397 | 11.792 | 12.292 | 12.946 | 13.909 | 15.665 |

FIG. 16

| Marker / Threshold | α=1.0 (0.990) | α=2.5 (0.975) | α=5.0 (0.950) | α=10.0 (0.900) |
|---|---|---|---|---|
| **Method 1** | | | | |
| Ferritin (log) | 58/2554 (2.27%) | 96/2554 (3.76%) | 176/2554 (6.89%) | 306/2554 (11.98%) |
| Serum Iron (log) | 89/2540 (3.50%) | 145/2540 (5.71%) | 211/2540 (8.31%) | 348/2540 (13.70%) |
| **Method 2** | | | | |
| Ferritin (log) | 171/2554 (6.70%) | 281/2554 (11.00%) | 397/2554 (15.54%) | 593/2554 (23.22%) |
| Serum Iron (log) | 94/2540 (3.70%) | 147/2540 (5.79%) | 214/2540 (8.43%) | 350/2540 (13.78%) |
| **Method 3** | | | | |
| HB | 43/1356 (3.17%) | 66/1356 (4.87%) | 104/1356 (7.67%) | 177/1356 (13.05%) |
| GR | 34/1353 (2.51%) | 70/1353 (5.17%) | 105/1353 (7.76%) | 179/1353 (13.23%) |
| HT | 21/1355 (1.55%) | 41/1355 (3.03%) | 70/1355 (5.17%) | 154/1355 (11.37%) |

METHOD FOR DETECTING ABNORMAL VALUES OF A BIOMARKER

CROSS-REFERENCE TO RELATED APPLICATIONS

The present application is a national phase entry under 35 U.S.C § 371 of International Application No. PCT/EP2018/081271 filed Nov. 14, 2018, which claims priority from European Patent Application No. 17306583.0 filed Nov. 14, 2017, all of which are hereby incorporated herein by reference.

FIELD OF THE INVENTION

The invention relates to clinical and biological monitoring and follow-up of individuals, such as the biological passport for athletes or medical files for patient, based on the individual and longitudinal monitoring of biomarkers. The invention allows to monitor any health event in a mammal.

Such monitoring or follow-up are used to identify abnormal behavior by comparing the deviation of an individual's biological sample to an established baseline. These comparisons may be done via different ways, but each of them requires an appropriate extra population to compute the significance levels, which is a non-trivial issue. Moreover, it is not necessarily relevant to compare the measures of a biomarker of a professional athlete to that of a reference population (even restricted to other athletes), and a reasonable alternative is to detect the abnormal values by considering only the other measurements of the same person.

The invention is therefore a tool to sort or identify individuals who should be subjected to further analysis. For instance, in medical studies, upon the result of the monitoring, a more detailed check-up of the patient can be run.

The method of the invention is also of interest for identifying a deficient measuring material by detecting abnormal value or series of values.

PRIOR ART

The systematic monitoring of biological variables over time allows for the early detection of physiological or biological changes. Such longitudinal studies are currently used for the identification of atypical biological observations in elite athletes.

This biological monitoring allows for determining the baseline value and its associated variability, provided a sufficient follow-up and a large cohort. Several sport organizations and researchers already developed such approaches in order to establish the biological profile of elite athletes for doping detection or medical concerns.

Several approaches for such a monitoring are known.

A well know method for identifying an abnormal value in longitudinal biomarker has been described in "Bayesian detection of abnormal values in longitudinal biomarkers with an application to TIE ratio", 2006, Sottas et al. in *Biostatitics.*

A known method, close to Sottas', called method 0, will now be disclosed.

Let $X_1, X_2, \ldots, X_n$ as n independent Gaussian random variables, with $X_i \sim N(\mu_i, \sigma^2)$, where N means a normal distribution. The method allows testing if the "new" observation $x_n$ is abnormal, given $x_1, x_2, \ldots, x_{n-1}$. They represent values of a biomarker of a person.

The usual way is to consider the following indicator:

$$T_n = \frac{X_n - \overline{X}_{n-1}}{\hat{\sigma}_{n-1}\sqrt{1 + \frac{1}{n-1}}}$$

Where $\overline{X}_{n-1}$ and $\hat{\sigma}_{n-1}$ are the empirical mean and variance of the sample $X_1, \ldots, X_{n-1}$, that is $$\overline{X}_{n-1} = \frac{1}{n-1}\sum_{k=1}^{n-1} X_k$$

$$\hat{\sigma}_{n-1}^2 = \frac{1}{n-2}\sum_{k=1}^{n-1}\left(X_k - \overline{X}_{n-1}\right)^2$$

Sottas quoted that, for small n, one cannot use this indicator to detect an abnormal value of $X_n$ by comparing the observed value $|t_n|$ of $|T_n|$ to the quantile $1-\alpha/2$ of the N(0,1) distribution.

However, if all the $\mu_i$ are equal, $T_n$ is distributed according to the Student(n−2) distribution, and the quantiles of this distribution can be used.

Given the observations $x_1, x_2, \ldots, x_{n-1}$ from the sample $X_1, X_2, \ldots, X_n$ there seems to be no good reason to consider only the case where the last observation could be abnormal given the previous ones.

A much more natural question is: how to detect an abnormal observation among all the observations? Even if one focuses only on the last observation, this question is of interest, because the presence of one (or more) abnormal observation in the past could lead to a wrong decision about the new observation $x_n$.

The first way is to iterate Method 0 as follows: one checks if $x_3$ is abnormal given $x_1, x_2$ then one checks if $x_4$ is abnormal given $x_1, x_2, x_3$ and so on up to the last step where one checks if $x_n$ is abnormal given $x_1, x_2, \ldots, x_{n-1}$.

This approach is not satisfactory for at least two reasons. First, the procedure is not invariant by time inversion (the forward and backward procedures can lead to two distinct results). Secondly, there is a multi-test problem, because n−2 tests are performed. If each test is performed at level $\alpha$ (alpha), then the level of the series of tests will be greater than $\alpha$. Moreover, the level correction seems difficult, since these tests are not independent, and the Bonferroni correction is known to be too conservative.

The practical consequences are the following: if no correction is made, then the series of tests is not well calibrated, with a type I error rate greater than announced, leading to an over-detection of false-positive values (specificity problem, this issue being more and more important as n increases). If the Bonferroni correction is performed, then again the series of tests is not well calibrated, with a type I error rate smaller than announced, leading to an under-detection of true positive values (sensitivity problem, this issue being more and more important as n increases)".

SUMMARY OF THE INVENTION

In a global aspect, the invention proposes a method for monitoring a health event in a mammal, comprising detecting at least one abnormal value within a series of values related to at least one biomarker, said biomarker corresponding to a physiological parameter or to the level of any biological or chemical entity measured from a biological sample of said mammal, the series of values ($x_1, x_2, \ldots, x_n$ related to said at least one biomarker being obtained from independent variables ($X_1, X_2, \ldots, X_n$) normally distributed (according to $N(\mu_x,\sigma^2)$);

said method comprising the following steps of:

E1: determining from each biological sample collected at different periods of time from said mammal, a value related to said at least one biomarker thereby acquiring a series of values ($x_1, x_2, \ldots, x_n$) related to said biomarker, E2: storing the series of values ($x_1, x_2, \ldots, x_n$) on a database stored in a memory;

said method comprising the following steps run with a processor that can retrieve data from the database in the memory:

E3: calculating, for the whole series of values of step E2 a single value $t_n$ of an indicator ($T_n$), said indicator ($T_n$) being based on a studentized form ($R_{n,i}$) of the variables ($X_1, X_2, \ldots, X_n$), said calculation consisting of extracting the maximum observed value ($t_n$) of the studentized form ($R_{n,i}$) calculated for each value of the series of values ($x_1, x_2, \ldots, x_n$), E4: comparing the observed value ($t_n$) of the indicator ($T_n$) to the quantile ($c_{\alpha,n}$) of the distribution of ($T_n$) said quantile being stored in the memory, E5: if the observed value ($t_n$) of the indicator ($T_n$) is above the quantile, reporting, on displaying means, a presence of an abnormal value in the series thereby indicating the occurrence of a health event for said mammal.

To summarize, the claimed method allows for a single detection rule, thus avoiding the above mentioned multi-test issues that would occur by testing if each new value is abnormal.

Besides, there is no need for comparison to values of a test population that can be considered as normal. Indeed, at the end of step E5, no decision is made towards a particular clinical picture: the single information that pops out is that the series contains a value "abnormal" compared to the other values of the series. This allows to expect a gain in specificity, intra individual variability being lower than the inter individual variability, let alone the issue of the actual relevance of the use of a standard (e.g. an athlete cannot be compared with standard population).

The method can comprise the further step of

E6: identifying from the series of values reported in step E2 at least one value being considered as abnormal, and E7: reporting on displaying means that at least one abnormal value.

In a first aspect, the method comprises the following features:

- a single series $x_1, x_2, \ldots, x_n$ of n values is stored on the database,
- n is the number of variables,
- $X_1, X_2, \ldots, X_n$ represent the n variables,
- the studentized form is a studentized residual expressed as:

$$R_{n,i} = \frac{X_i - \overline{X}_{n,-i}}{\hat{\sigma}_{n,-i}\sqrt{1 + \frac{1}{n-1}}}$$

the indicator $T_n$ is expressed as:

$$T_n = \max_{i \in \{1, \ldots, n\}} |R_{n,i}|$$

-continued where $$\overline{X}_{n,-i} = \frac{1}{n-1}\sum_{k=1,k\neq i}^{n-1} X_k$$

$$\hat{\sigma}^2_{n,-1} = \frac{1}{n-2}\sum_{k=1,k\neq i}^{n-1} \left(X_k - \overline{X}_{n,-i}\right)^2$$

For that aspect of the invention, a relevant table of quantiles of the distribution of $T_n$ is table 1.

This first aspect can also be expressed under a multivariate extension with the following features:

- a single series $x_1, X_2, \ldots, X_n$ of n values is stored on the database,
- n is the number of variables of dimension d,
- $X_1, X_2, \ldots, X_n$ represent the variables, where $X_i \sim N(\mu_i, C)$ and C, the covariance matrix is assumed to be invertible,
- the studentized form is expressed as a normalized length of the residual vector:

$$R_{n,i} = \frac{n-1}{nd}\left(X_i - \overline{X}_{n,-i}\right)' C_{n,-i}^{-1}\left(X_i - \overline{X}_{n,-i}\right)$$

where the notation z' means the transpose of the vector Z, the indicator $T_n$ is expressed as:

$$T_n = \max_{i \in \{1, \ldots, n\}} R_{n,i}$$

$$\overline{X}_{n,-i} = \frac{1}{n-1}\sum_{k=1,k\neq i}^{n-1} X_k$$

$$C_{n,-i} = \frac{1}{n-1-d}\sum_{k=1,k\neq i}^{n-1} \left(X_k - \overline{X}_{n,-i}\right)\left(X_k - \overline{X}_{n,-i}\right)'$$

For that aspect of the invention, a relevant table of quantiles of the distribution of $T_n$ is table 1b or 1c (for d=2 and d=3).

In a second aspect, the method comprises the following features:

- a single series $x_1, x_2, \ldots, x_n$ of n values is stored on the database,
- n is the number of variables,
- $X_1, X_2, \ldots, X_n$ represent the variables,
- $\varphi$ is the collection of all possible intervals I of consecutive integers included in $\{1, \ldots, n\}$ with length $1 \leq |I| < n$, $\{1, \ldots, n\} = I \cup \bar{I}$ and $I \cap \bar{I} = \phi$,
- the studentized form is expressed as:

$$R_{n,I} = \frac{\overline{X}_I - \overline{X}_{\bar{I}}}{\hat{\sigma}_{n,I}\sqrt{1 + \frac{1}{n-1}}}$$

the indicator $T_n$ is expressed as:

$$T_n = \max_{I \in \varphi} |R_{n,I}|$$

-continued where $$\overline{X}_I = \frac{1}{|I|}\sum_{k\in I} X_k$$

$$\overline{X}_{\overline{I}} = \frac{1}{n-|I|}\sum_{k\in \overline{I}} X_k$$

$$\hat{\sigma}^2_{n,I} = \frac{1}{n-2}\left(\sum_{k\in I}(X_k-\overline{X}_I)^2 + \sum_{k\in\overline{I}}(X_k-\overline{X}_{\overline{I}})^2\right)$$

For that aspect of the invention, a relevant table of quantiles of the distribution of $T_n$ is table 2.

In a third aspect, the method comprises the following features:

two series of $n_1$ and $n_2$ values are stored on the database (DB), $x_1, x_2, \ldots, x_{n_1}$ and $y_1, y_2, \ldots, y_{n_2}$, the studentized forms are studentized residuals expressed as:

$$R_{n_1,i} = \frac{X_i - \overline{X}_{n_1,-i}}{\hat{\sigma}_{X,-i,Y}\sqrt{1+\frac{1}{n_1-1}}}$$

and $$R_{n_2,j} = \frac{Y_j - \overline{Y}_{n_2,-j}}{\hat{\sigma}_{Y,-j,X}\sqrt{1+\frac{1}{n_2-1}}}$$

the indicator $T_n$ is expressed as:

$$T_n = \max\left\{\max_{i\in\{1,\ldots,n_1\}}|R_{n_1,i}|,\ \max_{j\in\{1,\ldots,n_2\}}|R_{n_2,j}|\right\}$$

where $$\overline{X}_{n_1,-i} = \frac{1}{n_1-1}\sum_{k=1,k\neq i}^{n_1} X_k$$

$$\overline{Y}_{n_2,-j} = \frac{1}{n_2-1}\sum_{k=1,k\neq j}^{n_2} Y_k$$

$$\hat{\sigma}^2_{X,-i,Y} = \frac{1}{n-3}\left(\sum_{k=1,k\neq i}^{n_1}(X_k-\overline{X}_{n_1,-i})^2 + \sum_{k=1}^{n_2}(Y_k-\overline{Y}_{n_2})^2\right)$$

$$\hat{\sigma}^2_{Y,-j,X} = \frac{1}{n-3}\left(\sum_{k=1}^{n_1}(X_k-\overline{X}_{n_1})^2 + \sum_{k=1,k\neq j}^{n_2}(Y_k-\overline{Y}_{n_2,-j})^2\right)$$

For that aspect of the invention, a relevant the table of quantiles of the distribution of $T_n$ is table 3.

This third aspect can also be expressed under a multivariate extension with the following features:

two series of $n_1$ and $n_2$ values are stored on the database (DB), $x_1, x_2, \ldots, x_{n_1}$ and $y_1, y_2, \ldots, y_{n_2}$, n is the number of variables of dimension d, $X_1, X_2, \ldots, X_{n_1}$ and $Y_1, Y_2, \ldots, Y_{n_2}$ represent the variables, where $X_i \sim N(\mu_{x_i}, C)$, $Y_j \sim N(\mu_{Y_j}, C)$ and C, the covariance matrix is assumed to be invertible, the studentized form is expressed as a normalized length of the residual vector:

$$R_{n_1,i} = \frac{n_1-1}{n_1 d}(X_i-\overline{X}_{n_1,-i})' C^{-1}_{X,-i,Y}(X_i-\overline{X}_{n_1,-i})$$

$$R_{n_2,j} = \frac{n_2-1}{n_2 d}(Y_j-\overline{Y}_{n_2,-j})' C^{-1}_{Y,-j,X}(Y_j-\overline{Y}_{n_2,-i})$$

the indicator $T_n$ is expressed as:

$$T_n = \max\left\{\begin{matrix}\max_{i\in\{1,\ldots,n_1\}} R_{n_1,i}\\ \max_{j\in\{1,\ldots,n_2\}} R_{n_2,j}\end{matrix}\right\}$$

where $$\overline{X}_{n_1,-i} = \frac{1}{n_1-1}\sum_{k=1,k\neq i}^{n_1} X_k$$

$$\overline{Y}_{n_2,-j} = \frac{1}{n_2-1}\sum_{k=1,k\neq j}^{n_2} Y_k$$

$$C_{X,-i,Y} = \frac{1}{n-2-d}\left(\sum_{k=1,k\neq i}^{n_1}(X_k-\overline{X}_{n_1,-i})(X_k-\overline{X}_{n_1,-i})' + \sum_{k=1}^{n_2}(Y_k-\overline{Y}_{n_2})(Y_k-\overline{Y}_{n_2})'\right)$$

$$C_{Y,-j,X} = \frac{1}{n-2-d}\left(\sum_{k=1}^{n_1}(X_k-\overline{X}_{n_1})(X_k-\overline{X}_{n_1})' + \sum_{k=1,k\neq j}^{n_2}(Y_k-\overline{Y}_{n_2,-j})(Y_k-\overline{Y}_{n_2,-j})'\right)$$

In the uni-variate case, Method 1 of the invention can be applied with at least three observations per individual. This is of course a (rather mild) restriction of the method but, on another hand, it can be applied to any sequence of independent Gaussian outcomes, without the help of an extra cohort to determine an appropriate a priori distribution.

It can be applied to any sequence of independent Gaussian outcomes, without the help of an extra cohort to determine an appropriate a priori distribution. That is to say, there is no need to have a predetermined known mean value or standard value (or values) of a biomarker within a population to apply the method. Besides the above-mentioned expectation of a gain in specificity in detecting abnormal variation by overcoming the issues in link with multitests, it has also an interest in term of cost of the study (no need for creating or buying standard values dataset) and reliability (relevance of the comparison of individual data with the corresponding data of a cohort).

The method of the invention can be applied to independent and normally distributed random variables, for series with at least three observations. This last point is not a strong limitation, since today's follow-ups often include more than three observations, and the sampling rate is increasing over the years. These methods can be continued with further investigations carried out by a medical staff in order to shed light on detected abnormal follow-ups.

The method can be improved to include additional periodic environmental effects, such as training at altitude. Practical applications include detecting abnormal values in elite athletes' or sport animal follow-ups for clinical or anti-doping purposes, and in individual's routine health check-up. It can also be useful in detecting pathological values in clinical follow-ups of subject based on individual rather than population-based thresholds. However, in that latest case the method is not aimed at identifying any disease for curative purpose, but merely to identify any potential health issue for the individual that would afterwards need further care or medical analysis to obtain a diagnosis by the physician.

The method may comprise the following steps:

- a step ES of running a Shapiro test on the stored values $(x_1, x_2, \ldots, x_{n_i})$ to check if the variables are normally distributed,
- a step ET of applying a function to the values to turn them into normally distributed variables, such as a log transformation.

The invention also relates to a program for computer comprising code lines to be executed by a processor, said code lines being configured to operate a method as disclosed previously from its step E2 to E4. The code lines may also be configured to run the different aspects of the method disclosed previously and/or run steps ES, ET.

The invention also relates to a system for monitoring a health event in a mammal, comprising detecting at least one abnormal value within a series of values related to at least one biomarker, said biomarker corresponding to a physiological parameter or to the level of any biological or chemical entity measured from a biological sample of said mammal, the system comprising:

- a database stored on a memory, the database comprising at least a series of values $(x_1, x_2, \ldots, x_n)$ related to said at least one biomarker being obtained from independent variables $(X_1, X_2, \ldots, X_n)$ normally distributed (according to $N(\mu_x,\sigma^2)$);

the values representing the evolution of the biomarker at different period of times, the values $(x_1, x_2, \ldots, x_n)$ of the biomarker being obtained from independent variables $(X_1, X_2, \ldots, X_n)$ normally distributed $N(\mu_x,\sigma^2)$,

- a processor comprising:
  - calculating means to calculate, for the whole series of values $(x_1, x_2, \ldots, x_n)$ stored in the database (DB), a single value $(t_n)$ of an indicator $(T_n)$, said indicator $(T_n)$ being based on a studentized form $(R_{n,i})$ of the variables $(X_1, X_2, \ldots, X_n)$, said calculation consisting of extracting the maximum value $(t_n)$ of the studentized residual form $(R_{n,i})$ calculated for each value of the series $(x_1, x_2, \ldots, x_n)$,
  - comparing means to compare the observed value $(t_n)$ of the indicator $(T_n)$ to the quantile $(c_{\alpha,n})$ of the distribution of $(T_n)$,
  - instruction means to instruct displaying means to report, or reporting means to report on displaying means, a presence of an abnormal value in the series, if the observed value $(t_n)$ of the indicator $(T_n)$ is above the quantile.

The system can also comprise acquisition means configured to acquire a series of values related to at least one biomarker and store them on a database stored in a memory and/or displaying means to receive the instructions of the processor.

The least one biomarker represented by the series of values may be chosen in the following list: ferritin, serum iron, hemoglobin, erythrocyte count, hematocrit levels, complete blood count, platelets, reticulocytes, soluble transferrin receptor, vitamin B9 in red blood cell, blood sugar, cholesterol, triglycerides, serum glutamic oxaloacetic transaminase (SGOT), serum glutamate pyruvate transaminase (SGPT), gamma-glutamyltransferase (γ-GT), lactate dehydrogenase (LDH), bilirubin, electrolytes (e.g. $Na^+$, $Cl^-$, $K^+$, $HCO3^-$, $Ca2^+$, $Mg2^+$), alkaline phosphatases Magnesium in red blood cells, creatinine, androstenedione, urea, uric acid, haptoglobin, C-reactive protein (CRP), transthyretin, orosomucoid, creatine phosphokinase (CPK), inorganic phosphate (PO4), thyroid-stimulating hormone (TSH), testosterone, cortisol, erythropoietin (EPO), ferritin, luteinizing hormone (LH), Insulin-like growth factor 1 (IGF-1), osteocalcin, calcifediol (25 OHD3).

BRIEF DESCRIPTION OF THE DRAWINGS

The following figures are given as a complement to understand the invention in a non-limitative way:

FIG. 5 illustrates the frequency of abnormal series for each biomarker and methods according different embodiments of the invention ($\alpha$=5%), FIG. 8 to FIG. 15 show tables 1 to 3 illustrating the value of the quantile for the different disclosed embodiments. Table 1 includes three tables 1a, 1b, 1c.

FIG. 16 illustrates the frequency of abnormal series for each biomarker and methods according different embodiments of the invention for $\alpha$=1.0, 2.5, 5.0 or 10.0% (number of abnormal series/total of series (Percentage of abnormal series))

DETAILED DESCRIPTION

Figure 1:
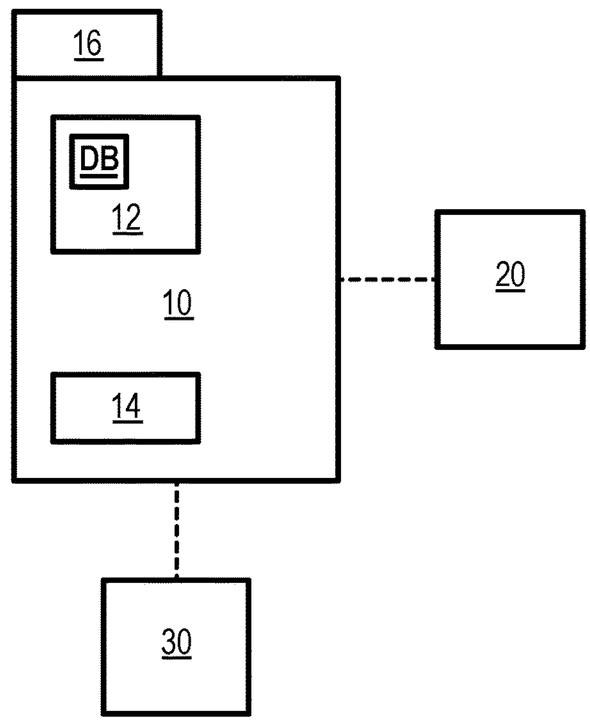
FIG. 1 illustrates a set-up to run the invention.

In the biological field, working under the assumptions that the biomarkers can be represented as independent variables is true. A study by Sottas (Pierre-Edouard Sottas, Norbert Baume, Christophe Saudan, Carine Schweizer, Matthias Kamber, Martial Saugy; Bayesian detection of abnormal values in longitudinal biomarkers with an application to T/E ratio, *Biostatistics*, Volume 8, Issue 2, 1 Apr. 2007, Pages 285-296) showed that after three days, no correlation can be observed between two values of a biomarker.

In the case of blood sample for instance, the average sampling rate is of the order of several months.

"Biomarker" correspond for the present invention to the level of any biological or chemical entity measured from a biological sample of a mammal. Complementarily, biomarkers can also represent physiological parameters of the mammal, which have to be first collected and gathered and then extemporaneously applied in the method according to the invention, thereby not requiring any interaction with the body of the subject.

The biomarker(s) is (are) for instance one or more of biomarker(s) chosen in the following list: the concentrations of ferritin, serum iron, hemoglobin, erythrocyte count, hematocrit levels, complete blood count, platelets, reticulocytes, soluble transferrin receptor, vitamin B9 in red blood cell, blood sugar, cholesterol, triglycerides, serum glutamic oxaloacetic transaminase (SGOT), serum glutamate pyruvate transaminase (SGPT), gamma-glutamyltransferase (γ-GT), lactate dehydrogenase (LDH), bilirubin, electrolytes (e.g. $Na^+$, $Cl^-$, $K^+$, $HCO3^-$, $Ca2^+$, $Mg2^+$), alkaline phosphatases magnesium in red blood cells, creatinine, androstenedione, urea, uric acid, haptoglobin, C-reactive protein (CRP), transthyretin, orosomucoid, creatine phosphokinase (CPK), inorganic phosphate (PO4), thyroid-stimulating hormone (TSH), testosterone, cortisol, erythropoietin (EPO), ferritin, luteinizing hormone (LH), Insulin-like growth factor 1 (IGF-1), osteocalcin, calcifediol (25 OHD3).

In a particular aspect, the biomarker(s) is (are) for instance one or more of biomarker(s) chosen in the following list: the concentrations of ferritin, serum iron, hemoglobin, erythrocyte count, hematocrit levels.

Biomarkers corresponding to the level of any biological or chemical entity are measured from a sample of a subject, for example, a fluid sample as blood, plasma, serum or urine.

Examples of basic physiological parameters of the art are ECG, heart rate, respiratory rate, respiratory volume, body temperature, blood pressure, electromyogram measured by any technical mean of the art.

The terms "health event" correspond to any situation related to the state of health of a subject, being suspected from the detection using the method of the invention of an abnormal value in a series for one or more biomarker.

In the present description, reference will be made to a human subject but the disclosed method applies to any mammal.

The rationale of the invention is based on the fact that the joint distribution of some appropriate residuals is free of the parameters in a Gaussian context.

In a first step E1, several biological samples of the mammal, collected at different periods of time are analyzed. For each sample, a value related to at least one of the precited biomarker is acquired. Therefore, for each mammal, a series of values $x_1, x_2, \ldots, x_n$ is determined in step E1.

Those values represent the evolution of the biomarker in function of the time. Typically, index 1 refers to the oldest measurement while index n generally refers to the latest one.

Step E1 can encompass the in vitro analysis run in labs on the blood sample. In a particular aspect step E1 also encompasses the tests run on the individual to obtain a value of a biomarker, more particularly a biomarker related to a physiological parameter. In another particular aspect, step E1 does not encompass the test run on the individual but only the gathering and formatting of the data related to said biomarkers in order to allow their processing in the further steps of the method. In a more particular aspect, step E1, when related to a physiological parameter does not encompass the test run on the individual but only the gathering and the formatting of the data related to said physiological parameter.

In second step E2, the series of values $x_1, x_2, \ldots, x_n$ are stored on a database DB. This database preferably contains several series related to different biomarkers As show on FIG. 1, which illustrates a system according to an embodiment of the invention, the database is stored on a memory 12, which can be ROM or RAM, of a calculation unit 10. The calculation unit 10 also comprises processing means 14, such as a processor, to compute data from the database DB of the memory 12. To implement data in the memory 12, the calculation unit 10 comprises interface means 16. The processing means 14 comprises calculation means, comparing means and instruction means (all of them can be included in the same processor for instance).

The system can also comprise acquisition means (sensors, laboratory materials, etc.) which can be used for during step E1.

The results obtained through the calculation unit 10 are shown on displaying means 20, for instance a screen. Communication between the calculation unit 10 and the displaying means 20 is achieved via a wire for instance (VGA, HMDI, etc.)

The calculation unit 10 can be a personal computer or a delocalized server (cloud computing) communicating with a local interface for instance through a network (ethernet, WIFI, etc.)

Before being computed by the processor according to the method that shall be disclosed herebelow, the series of values $x_1, x_2, \ldots, x_n$ can be treated to be in a proper shape in a step ET. Step ET will be illustrated later.

The database DB is updated with data obtained from different processes.

The method of the invention used the maximum of a "studentized" form. Several embodiments are going to be disclosed herebelow.

That method allows detecting an abnormal value (or an abnormal subseries of values) in a series of values.

The invention will be disclosed in details for the first embodiment. The other embodiments will be disclosed more briefly.

Figure 2:
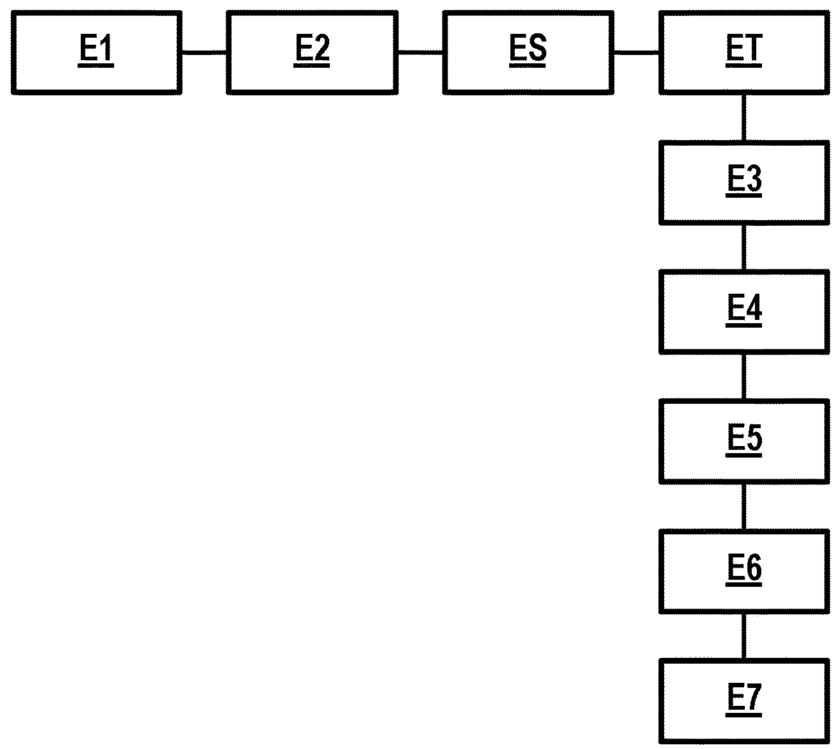
FIG. 2 illustrates the main steps of an embodiment of the invention.

FIG. 2 illustrates the main steps of a method according to an embodiment.

Method 1 of the Invention

In a first aspect of the invention, the method proposes a global test, defined by the following indicator:

$$T_n = \max_{i \in \{1, \ldots, n\}} |R_{n,i}|$$

Where $$R_{n,i} = \frac{X_i - \overline{X}_{n,-i}}{\hat{\sigma}_{n,-i}\sqrt{1 + \frac{1}{n-1}}}$$

$R_{n,i}$ being the studentized residual form $$\overline{X}_{n,-i} = \frac{1}{n-1} \sum_{k=1, k \neq i}^{n-1} X_k$$

$$\hat{\sigma}^2_{n,-i} = \frac{1}{n-2} \sum_{k=1, k \neq i}^{n-1} (X_k - \overline{X}_{n,-i})^2$$

In that embodiment, the studentized residual form $R_{n,i}$ is actually a studentized residual.

This method is based on the maximum of n (non independent) variables with Student(n−2) distribution.

Under the null hypothesis $H_0$, $\mu_1=\mu_2= \ldots =\mu_n=\mu$, the distribution of $T_n$ does not depend on the unknown parameters $\mu,\sigma^2$ and can therefore be tabulated.

Indeed, although an analytical resolution is not possible, a largely good enough precision can be obtained through tabulation (for instance twenty million tries per threshold are easily computable with standard computational means, to allow a $10^{-3}$ precision).

Once the indicators $T_n$ has been implemented, the processor 14 computes the calculus in a step E3. As a matter of fact, at least n operations are calculated: each value of student residuals form $R_{n,i}$ and then at least one operation to extract the maximum value $t_n$ of $T_n$.

According to that method, for one series of samples $x_1, x_2, \ldots, x_n$ representing the values of the variables $X_1, X_2, \ldots, X_n$ the step of calculation shall provide a single output, noted $T_n$.

The next step E4 is the comparison of the observed value $t_n$ of the indicator $T_n$ to a threshold. The threshold is taken from a quantile table, representing the distribution of $T_n$.

The quantile tables are typically precomputed and stored in the memory.

For a threshold α, it can be considered that the series (i.e. at least one value of the series) is abnormal if $t_n > c_{\alpha,n}$, where $c_{\alpha,n}$ is such that $P_n([c_{\alpha,n},\infty[=\alpha$.

Therefore the processor computes that comparison with the results $t_n$ obtained at the end of the former step E3.

In a step E5, the result of the comparison is displayed on the displaying means 20 if $t_n > c_{\alpha,n}$, where $c_{\alpha,n}$ is the quantile of order 1−α of the distribution of $T_n$. In other words, if the observed value $t_n$ of the indicator $T_n$ is above the quantile, a presence of an abnormal value in the series is reported on the displaying means, thereby indicating the occurrence of an health event for said mammal.

Table 1a provides values for the quantile of the distribution of $T_n$.

The method can be applied as soon as n≥3.

With the information of an abnormal value, application in the doping control or the medical follow-up of individuals are immediate.

In another embodiment this method can be equally applied to multivariate extension, that is when $X_1, X_2, \ldots, X_n$ are n independent $R^d$ valued random vector, where $X_i \sim N(\mu_i, C)$ and C (the covariance matrix) is assumed to be invertible.

To detect if a vector of the series is abnormal, indicator $T_n$ is implemented in the following way:

$$T_n = \max_{i \in \{1, \ldots, n\}} R_{n,i}$$

Where $$R_{n,i} = \frac{n-1}{nd}(X_i - \overline{X}_{n,-i})' C_{n,-i}^{-1}(X_i - \overline{X}_{n,-i})$$

$R_{n,i}$ being a kind of studentized residual form, more precisely a normalized length of the residual vector, z' being the transpose vector of vector z.

$$\overline{X}_{n,-i} = \frac{1}{n-1}\sum_{k=1,k\neq i}^{n-1} X_k$$

$$C_{n,-i} = \frac{1}{n-1-d}\sum_{k=1,k\neq i}^{n-1}(X_k - \overline{X}_{n,-i})(X_k - \overline{X}_{n,-i})'$$

Step E2 is identical, excepted for the indicators to be applied.

As previously explained, under the null hypothesis, $\mu_1 = \mu_2 = \ldots = \mu_n = \mu$, the distribution of $T_n$ does not depend on μ or C and can therefore be tabulated.

The comparison step E4 is the same and the displaying step E5 is also the same.

This method can be applied as soon as n≥d+2.

Table 1b or 1c provides values for the quantile of the distribution of $T_n$ (for d=2 and d=3).

The univariate case described before is just a specific case of the multivariate case (up to a square in the expression of $T_n$).

Method 2 of the Invention

A further implementation of the invention would be to detect a series of consecutive observations that are abnormal compared to the rest of the series.

Formally speaking, there is need to know if there is a set I={i, . . . , j} of consecutive integers, for which the expectations of the $X_k$, k∈I is different from the expectation of the other variables, that is $\mu_k = \mu_l = \mu_A$ if k, l do not belong to I and $\mu_k = \mu_l = \mu_B$ if k, l belong to I.

The rationale behind method 2 is the same as behind method 1. The maximum of a studentized form is calculated by the processor 14.

More precisely, the proposed indicator is $$T_n = \max_{i \in \varphi} |R_{n,I}|$$

Where φ is the collection of all possible intervals I included in {1, . . . , n} with length 1≤|I|<n, $\{1, \ldots, n\} = I \cup \bar{I}$ and $I \cap \bar{I} = \phi$ $$R_{n,I} = \frac{\overline{X}_I - \overline{X}_{\bar{I}}}{\hat{\sigma}_{n,I}\sqrt{1 + \frac{1}{n-1}}}$$

$$\overline{X}_I = \frac{1}{|I|}\sum_{k \in I} X_k$$

$$\overline{X}_{\bar{I}} = \frac{1}{n - |I|}\sum_{k \in \bar{I}} X_k$$

$$\hat{\sigma}_{n,I}^2 = \frac{1}{n-2}\left(\sum_{k \in I}(X_k - \overline{X}_I)^2 + \sum_{k \in \bar{I}}(X_k - \overline{X}_{\bar{I}})^2\right)$$

As the indicator is working on intervals I, the studentized form has been adapted from the studentized residual stricto sensu of Method 1.

Under the null hypothesis, again, the distribution of $T_n$ does not depend on the unknown parameters $\mu, \sigma^2$ and can be tabulated.

The comparison and displaying steps E4, E5 are similar to the ones previously disclosed.

If the comparison step E4 is positive, then it means that there is a subseries of consecutive values that can be considered as abnormal compared to the rest of the series.

Table 2 provides values for the quantile of the distribution of $T_n$.

Like method 1, method 2 can be extended to multivariate extension.

Method 3 of the Invention

At last, the method of the invention can be applied to two series of observations $x_1, x_2, \ldots, x_{n_1}, y_1, y_2, \ldots, y_{n_2}$. In that case, there is a need to know if one of these observations is abnormal given the other ones in the same subsample.

This method allows considering the case where there is an influence of season on the expectation of the variables.

Indeed, the behavior of the biomarkers may differ according to the period of the year (summer and winter for instance). The sample is thus split into two subsamples $x_1, x_2, \ldots, x_{n_1}$ and $y_1, y_2, \ldots, y_{n_2}$.

The proposed indicator is $$T_n = \max\left\{\max_{i\in\{1,\ldots,n_1\}}|R_{n_1,i}|, \max_{j\in\{1,\ldots,n_2\}}|R_{n_2,j}|\right\}$$

Where $$R_{n_1,i} = \frac{\overline{X}_i - \overline{X}_{n_1,-i}}{\hat{\sigma}_{X,-i,Y}\sqrt{1+\frac{1}{n_1-1}}}$$

$$R_{n_2,j} = \frac{\overline{Y}_j - \overline{Y}_{n_2,-j}}{\hat{\sigma}_{Y,-j,X}\sqrt{1+\frac{1}{n_2-1}}}$$

$R_{n_1,1}$, $R_{n_2,j}$ being studentized residuals, $$\overline{X}_{n_1,-i} = \frac{1}{n_1-1}\sum_{k=1,k\neq i}^{n_1} X_k$$

$$\overline{Y}_{n_2,-j} = \frac{1}{n_2-1}\sum_{k=1,k\neq j}^{n_2} Y_k$$

$$\hat{\sigma}^2_{X,-i,Y} = \frac{1}{n-3}\left(\sum_{k=1,k\neq i}^{n_1}(X_k - \overline{X}_{n_1,-i})^2 + \sum_{k=1}^{n_2}(Y_k - \overline{Y}_{n_2})^2\right)$$

$$\hat{\sigma}^2_{Y,-j,X} = \frac{1}{n-3}\left(\sum_{k=1}^{n_1}(X_k - \overline{X}_{n_1})^2 + \sum_{k=1,k\neq j}^{n_2}(Y_k - \overline{Y}_{n_2,-j})^2\right)$$

Under the null hypothesis again, the distribution of $T_n$ does not depend on the unknown parameters $\mu_A, \mu_B, \sigma^2$ and can therefore be tabulated.

Table 3 provides values for the quantile of the distribution of $T_n$.

This method can be applied as soon as $n_1 \geq 2$ and $n_2 \geq 2$

The same extension to multivariate cases also applies.

In that case, let us consider $X_1, x_2, \ldots, X_{n_1}$ and $Y_1, Y_2, \ldots, Y_{n_2}$ and two independent series of independent Gaussian $R^d$ valued random vectors with $X_i \sim N(\mu_{x_i}, C)$, $Y_j \sim N(\mu_{Y_j}, C)$ and C is assumed to be invertible.

The purpose is to detect if the vector $x_k$ or $y_l$ is abnormal given the other ones in the same subsample.

The following indicators is proposed $$T_n = \max\left\{\begin{matrix}\max_{i\in\{1,\ldots,n_1\}}|R_{n_1,i}|, \\ \max_{j\in\{1,\ldots,n_2\}}|R_{n_2,j}|\end{matrix}\right\}$$

Where $$R_{n_1,i} = \frac{n_1-1}{n_1 d}(X_i - \overline{X}_{n_1,-i})' C^{-1}_{X,-i,Y}(X_i - \overline{X}_{n_1,-i})$$

-continued $$R_{n_2,j} = \frac{n_2-1}{n_2 d}(Y_j - \overline{Y}_{n_2,-j})' C^{-1}_{Y,-j,X}(Y_j - \overline{X}_{n_2,-i})$$

$R_{n_1,i}$, $R_{n_2,j}$ being the normalized lengths of the residual vectors, $$\overline{X}_{n_1,-i} = \frac{1}{n_1-1}\sum_{k=1,k\neq i}^{n_1} X_k$$

$$\overline{Y}_{n_2,-j} = \frac{1}{n_2-1}\sum_{k=1,k\neq j}^{n_2} Y_k$$

$$C_{X,-i,Y} = \frac{1}{n-2-d}\left(\sum_{k=1,k\neq i}^{n_1}(X_k - \overline{X}_{n_1,-i})(X_k - \overline{X}_{n_1,-i})' + \sum_{k=1}^{n_2}(Y_k - \overline{Y}_{n_2})(Y_k - \overline{Y}_{n_2})'\right)$$

$$C_{Y,-j,X} = \frac{1}{n-2-d}\left(\sum_{k=1}^{n_1}(X_k - \overline{X}_{n_1})(X_k - \overline{X}_{n_1})' + \sum_{k=1,k\neq j}^{n_2}(Y_k - \overline{Y}_{n_2,-j})(Y_k - \overline{Y}_{n_2,-j})'\right)$$

Under the null hypothesis, $\mu_{x_1} = \ldots = \mu_{X_{n_1}} = \mu_X$ and $\mu_{Y_1} = \ldots = \mu_{Y_{n_2}} = \mu_Y$, the distribution of Tn does not depend on the unknown parameters $\mu_X$, $\mu_Y$, C and can be tabulated.

The comparison and displaying steps E4, E5 are the same as previously explained.

The table of the values for the quantile of the distribution of $T_n$ can be computed (not disclosed in the Tables here).

This method can be applied as soon as $n_1 \geq 2$ and $n_2 \geq 2$ and $n_2 \geq d+3$.

Figure 7:
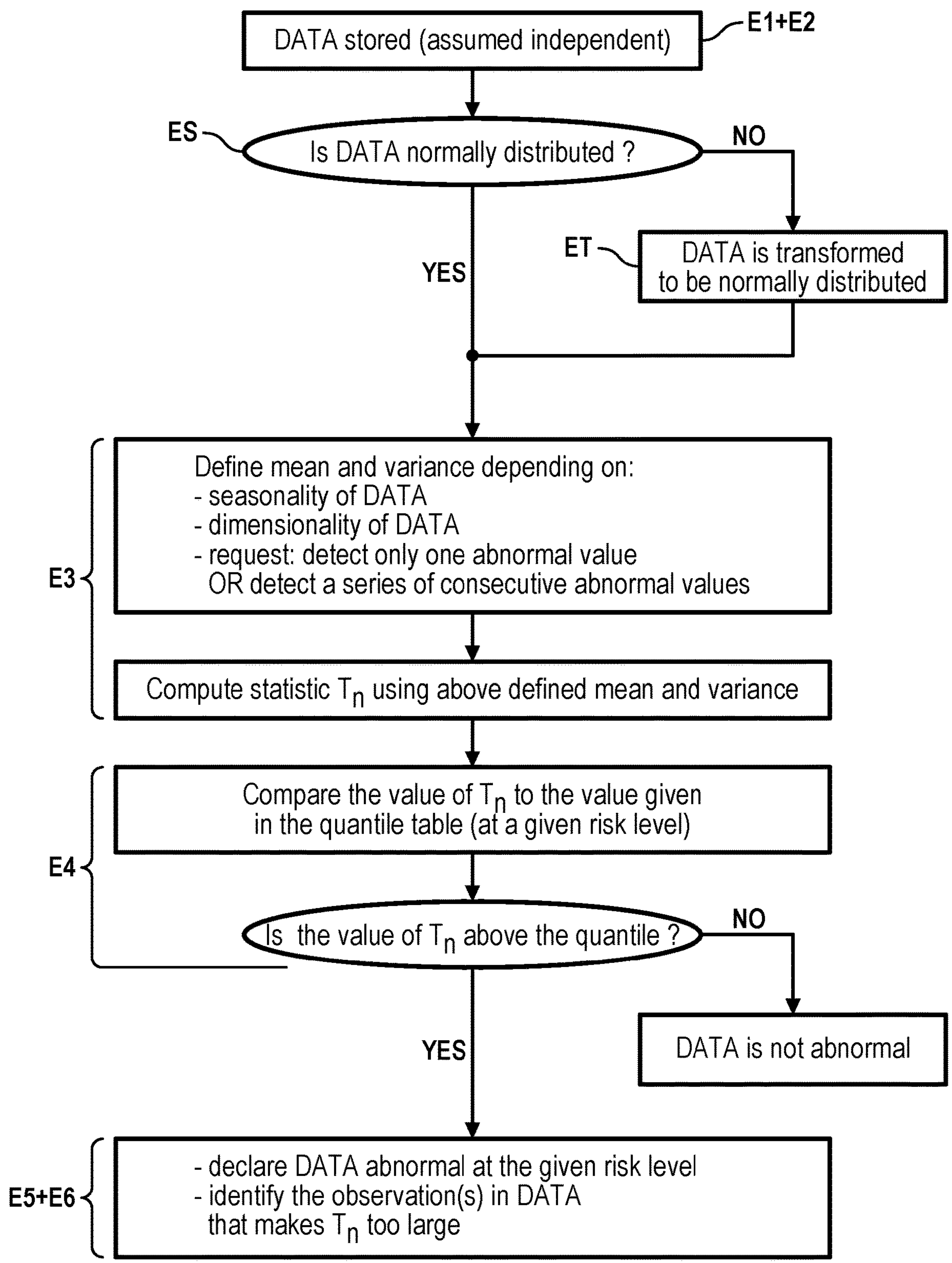
FIG. 7 illustrates a flow chart representing some steps of an embodiment according to the invention.

The steps of the different embodiments of the disclosed method are summarized in flow chart in FIG. 7.

Further Elements

To check that the variables are normally distributed, a Shapiro test can be run on the stored values (step ES). This step ES can be run during step E2 for instance, or between E2 and E3.

To ensure that some variables are normally distributed, some series are log-transformed in a further step ET. Any mathematical transformation that works would be applicable.

This step ET can be run during step E2 for instance, or between steps E2 and E3.

The computation of the quantiles is known for a skilled person and will not be disclosed here.

Once step E5 has been achieved and it is known whether or not an abnormal value (or a subseries of value) exists, that abnormal value can be identified from the series and extracted in step E6 and reported on the displaying means 20 in step E7.

The abnormal value is the value that maximizes the indicators $T_n$.

Step E5 and E6 are not resources-consuming since all the values of the indicators $T_n$, have already been computed.

The present invention comprises a new and simple method based on maxima of Z-scores that do not rely on the use of data from an external population (reference population). This method is extended to three Z-scores-based analyses for detecting abnormal values in a series of biological measures from an individual's sample with particular specificities. For example, making use of this invention, it is possible to assess the individual baseline while taking into account the seasonal changes that alter the values of biomarkers. The multivariate approach is also developed in order to avoid multi-test issues and to take care of the possible correlations between biomarkers.

As it will be disclosed below, the embodiments of the invention (Methods 1 to 3) have been tested on the follow-up of elite athletes and the results are in accordance with the expected false discovery rate, in most of the cases.

Performance of Method 1

This example shows how Method 1 detects an abnormal value when all the others are identically distributed.

$1\times10^6$ sequences consisting of n independent Gaussian random variables are simulated. The third random variable has distribution $N(\mu,1)$, with $\mu>0$, whereas all the other random variables have distribution $N(0,1)$. The simulations are performed for a number of observations n ranging from 4 to 15 and μ ranging from 0 to 10 with a step of 0.1.

The same procedure is used for the multivariate analysis, with d=2. The third random vector has distribution $n(\mu,C)$, whereas all the other random vectors have distribution $N(0,Id)$. Here $\tilde{u}=(\mu,\mu)$ with the same possible values of μ as in the uni-variate case, and the covariance matrix C is given by:

$$C=\begin{bmatrix} 1 & 0.5 \\ 0.5 & 1 \end{bmatrix}$$

Figure 3:
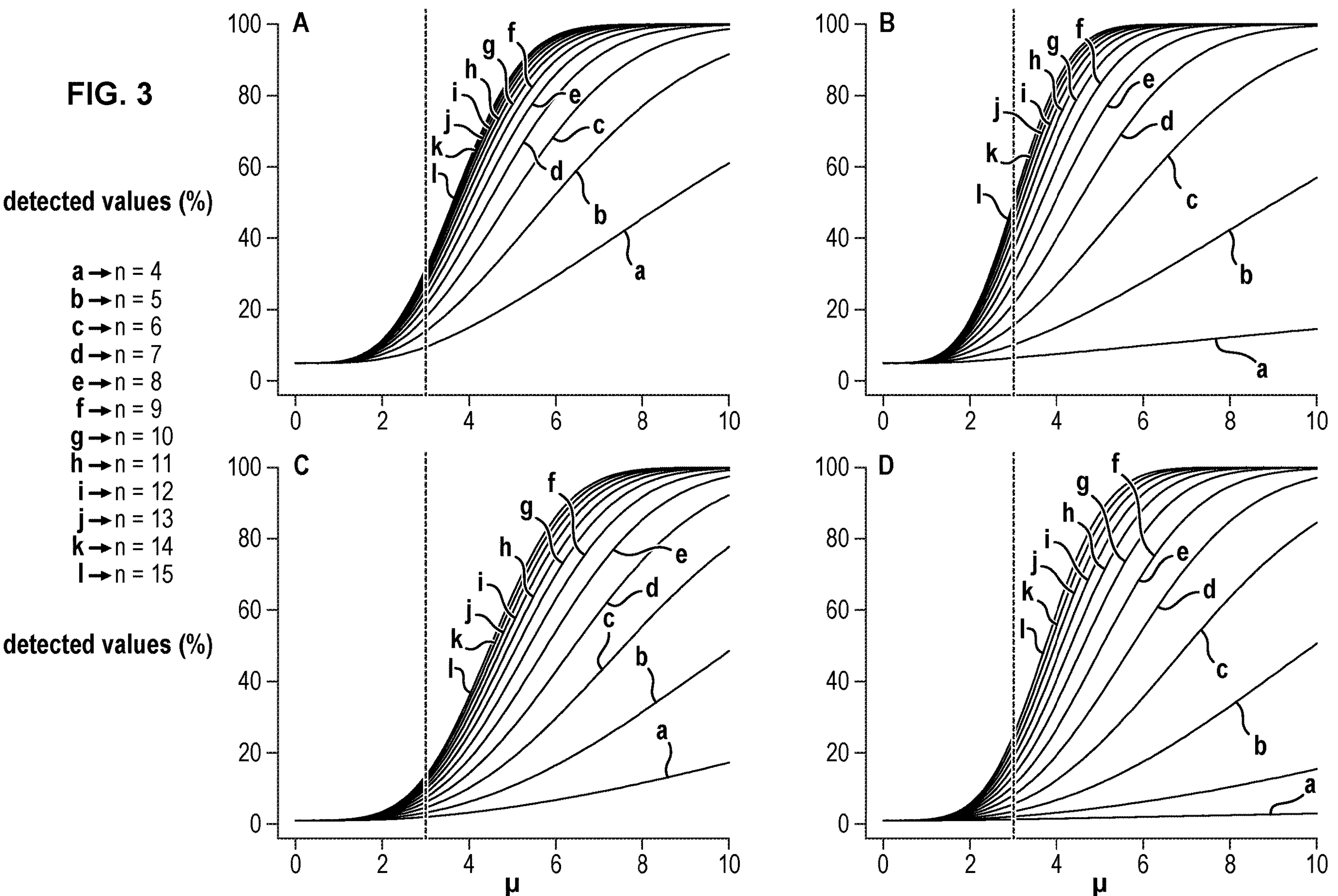
FIG. 3 illustrates the frequency of abnormal values detected by different methods according to embodiments of the invention.

The results are given in FIG. 3 (Method 1: sketches A and C and its multivariate extension: sketches B and D, as a function of μ and $\mu_d$ for the levels $\alpha=5\%$ (A,B) and $\alpha=1\%$ (C,D); the dash line $\mu=3$ is merely an indicator).

As expected, the power curve is increasing with n and μ. Percentages of abnormal sequences detected for n=9 and μ, respectively, equals to 2, 4 and 6 are 10.53%, 51.06% and 90.57%.

Application to Football Players

After obtaining the approval of the Institutional Ethics Committee the 3 methods were applied to a database of elite soccer players.

A) Application to blood biomarkers from a sample of 2577 soccer players.

It consists of five typical biological markers from 2577 male soccer players from the French elite leagues 1 & 2. Biomarkers include concentrations of ferritin (μmol/L), serum iron (μmol/L), hemoglobin (g/L), erythrocytes (T/L) and hematocrit levels (%).

The biomarkers were collected every six months in July/August and in January/March from 2006 to 2012 for a total of twelve collections. The large interval between two measures (around six months) allowed for independent sampling (Sharpe and others (2006)). Only the series for which at least five measurements over the twelve possible measurements were available had been analyzed, totalizing: ferritin & serum iron levels from 757 players, erythrocytes & hematocrit levels from 799 players and for hemoglobin levels from 807 players because of the high number of transfers between clubs, injuries and the progressive inclusion of new clubs in the elite league.

Moreover, a technical issue with the sampling instrument resulted in the loss of the data in the markers of the 2009 July/August collection. According to Custer and others (1995); Tufts and others (1985) the measure of the ferritin and serum iron have a log-normal distribution, so the logarithm of the observations for these two biomarkers was used (step E1).

The individual series of biomarkers must comply with the conditions related to the normal distribution: each individual and each biomarker, step ES was conducted and a Shapiro test was achieved to confirm that it is not unrealistic to assume that the observations are drawn from a normal sample.

Some non-detailed analysis on the data set is run to conclude that only ferritin and serum iron are eligible for methods 1 and 2. For the other biomarkers, the third method can be applied as they were found subjected to a significant seasonal variability.

Figure 4:
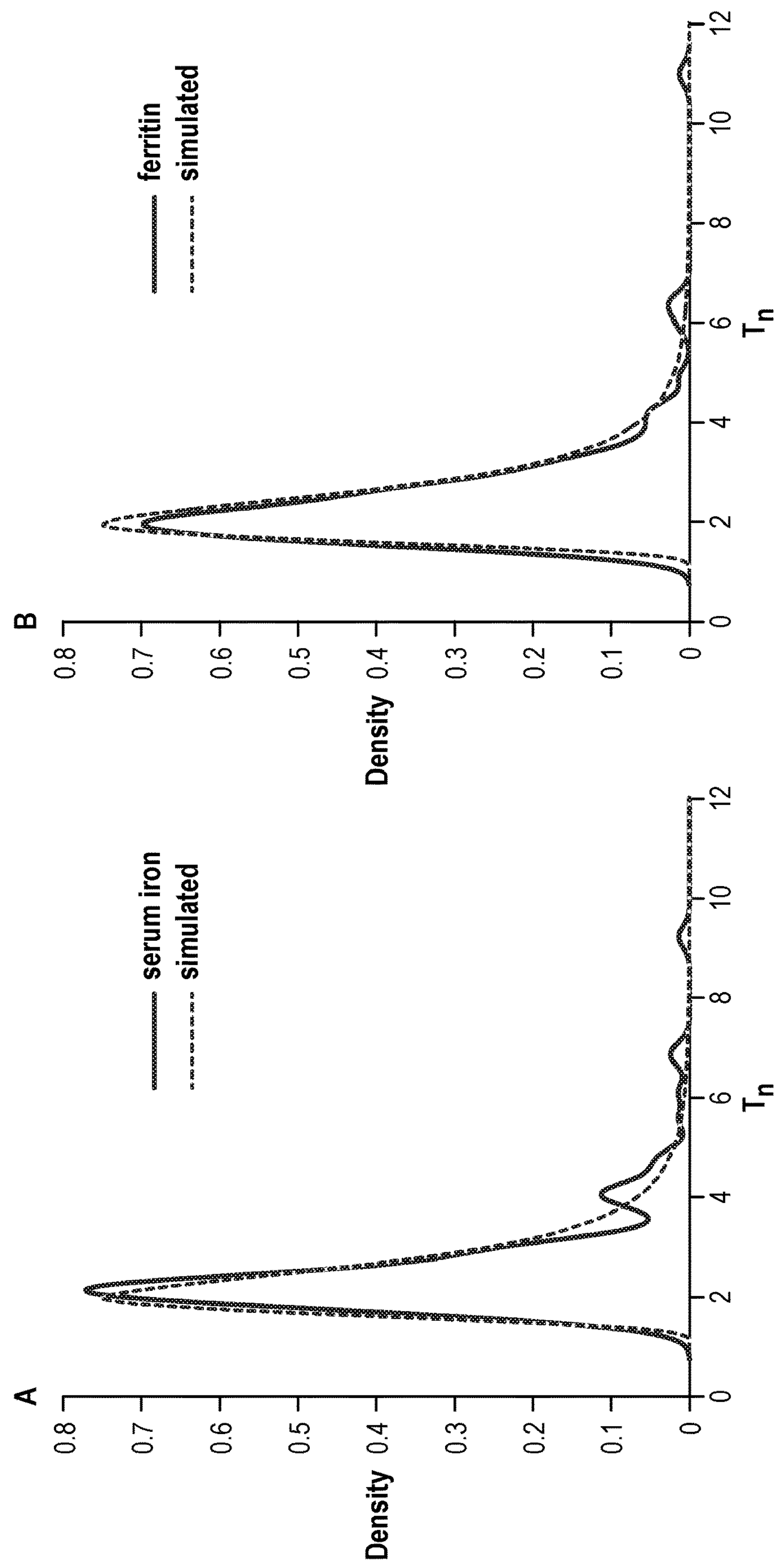
FIG. 4 illustrates the distribution of estimated $T_n$ of an embodiment of the invention versus the normal distribution for erythrocyte count and hematocrit.

For the two markers ferritin and serum iron, the empirical distribution of $T_n$ (Method 1) is close to the theoretical one under H0 (see FIG. 4: distribution of estimated $T_n$ with its correspond simulated distribution $10^6$ individuals, gray curve) for erythrocytes (A) and hematocrit (B)). This confirms that the quantiles of the theoretical distribution of $T_n$ can be used to detect abnormal values on our dataset.

The frequency of abnormal series detected by the procedures are reported in FIG. 5 for a level $\alpha=5\%$.

Most of the results are not too far from the expected false discovery rate: between 5% and 6.7% for Ferritin/Method 1, Serum iron/Method 2 and all three others biomarkers for Method 3; 8.19% for Serum Iron/Method 1. However, the percentage of abnormal sub-series for Ferritin/Method 2 is close to 11%, hence significantly different from the expected level $\alpha=5\%$. Though further analyses are required to shed light on these series, and notably on the actual cause for these abnormal values, method of the invention is found effective in detecting abnormal values within series of data related to biomarkers. Indeed, the same percentage of abnormal values is obtained by applying the multi-variate version of Method 1 or by applying the two uni-variate procedures (6.9% in both cases).

Figure 6A:
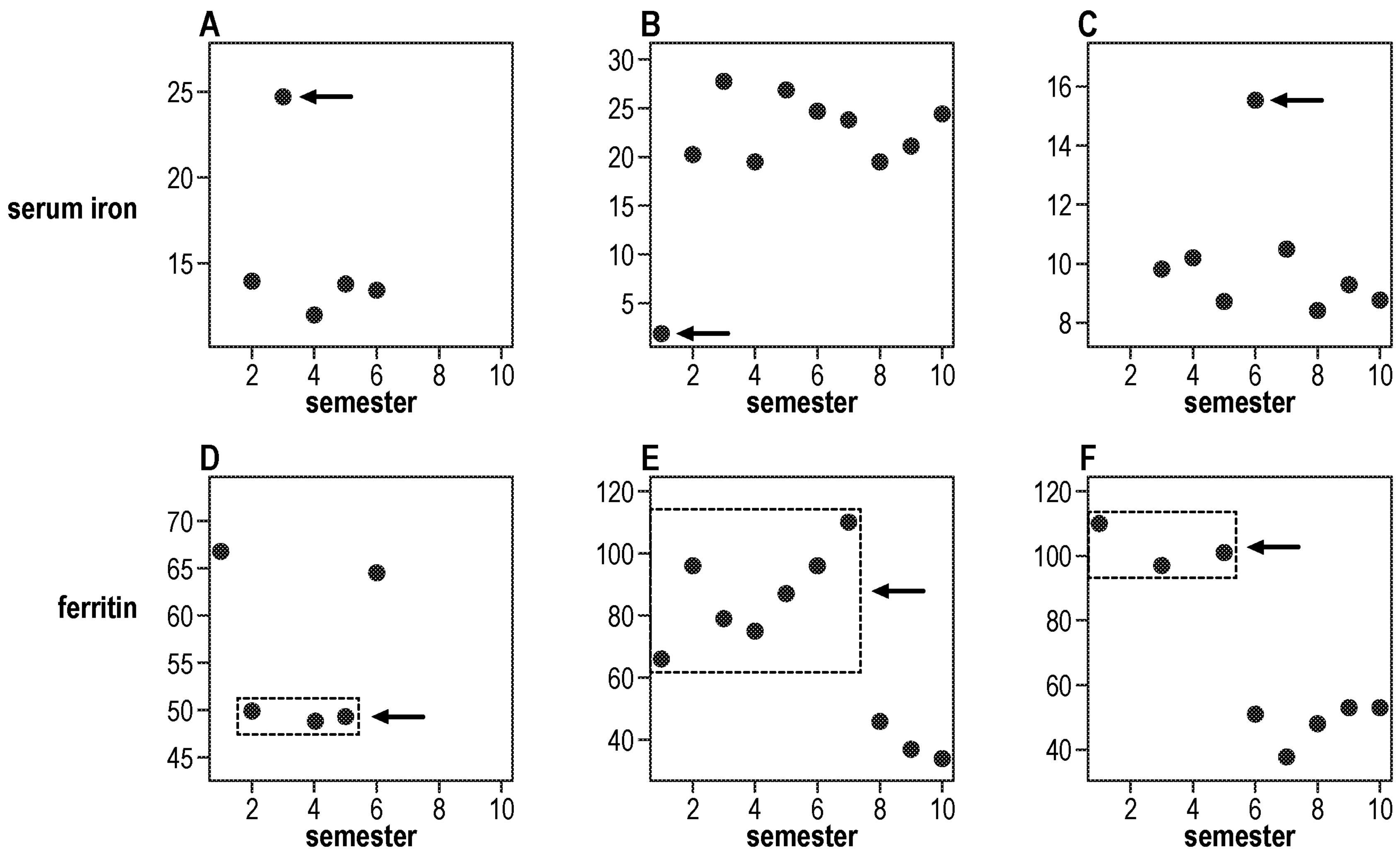
FIG. 6*a* and FIG. 6*b* illustrate examples of results for the different embodiments of the invention, for several biomarkers.
Figure 6B:
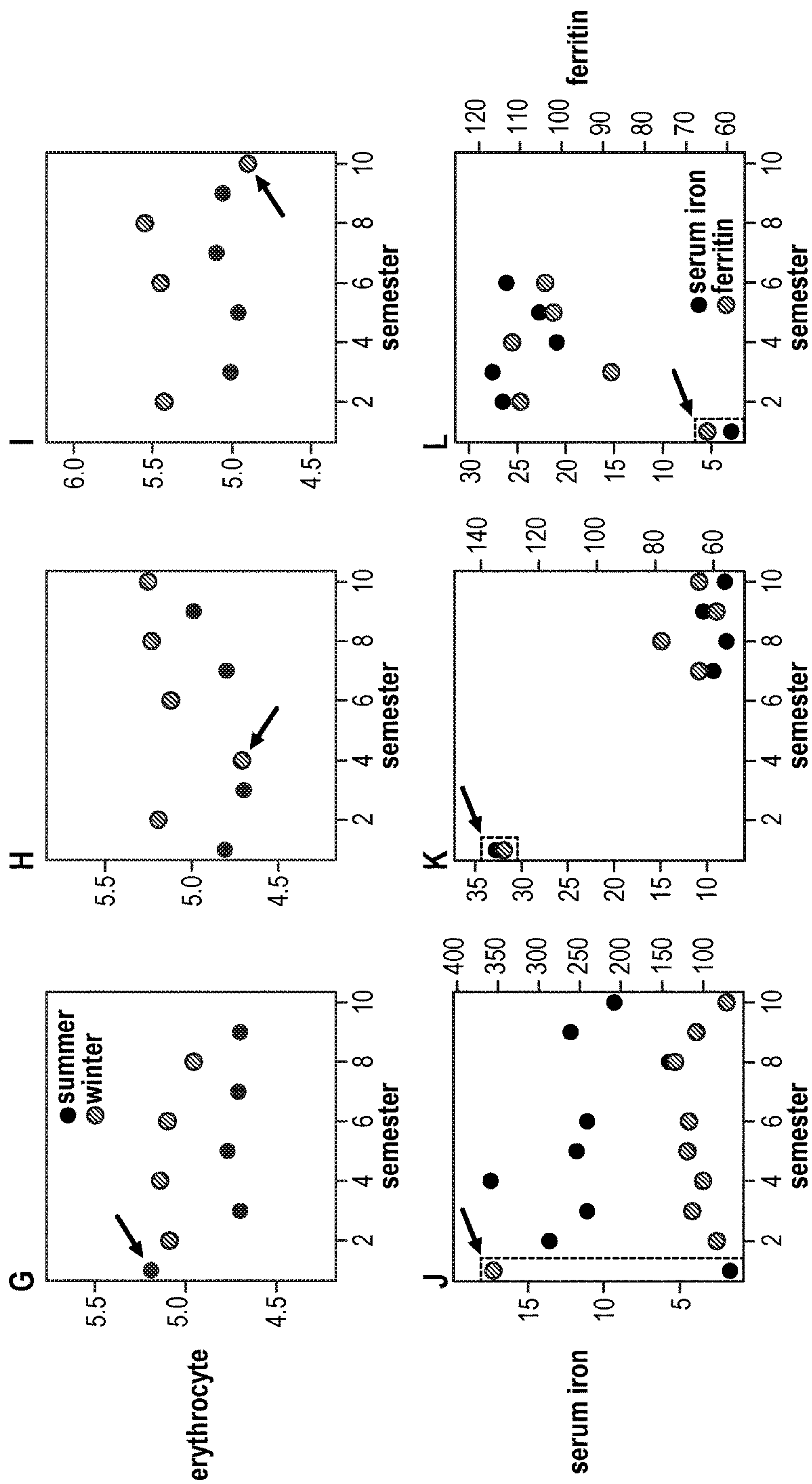

In FIG. 6*a* and FIG. 6*b*, some examples are given of abnormal observations detected by the three methods, for different biomarkers: method 1 (A, B, C), Method 2 (D, E, F) and Method 3 (G, H, I); panels J, K, L show the multivariate version of Method 1. The y-axis represents the biomarker values (units depend on the biomarker), and the x-axis corresponds to time (semesters).

B) Application to blood biomarkers from a sample of 3936 soccer players and blind analysis validation study.

As above, concentrations of ferritin (μmol/L), serum iron (μmol/L), hemoglobin (g/L), erythrocytes (T/L) and hematocrit levels (%) were five typical biological markers from 3936 male soccer players from the French elite leagues 1 & 2 collected from 21/06/2005 to 05/10/2017.

The frequency of abnormal series detected by the procedures are reported in FIG. 16 for a level $\alpha=1$, 2.5, 5 or 10%. The more alpha is high, the more the number of supposed abnormal series is important.

Figure 17:
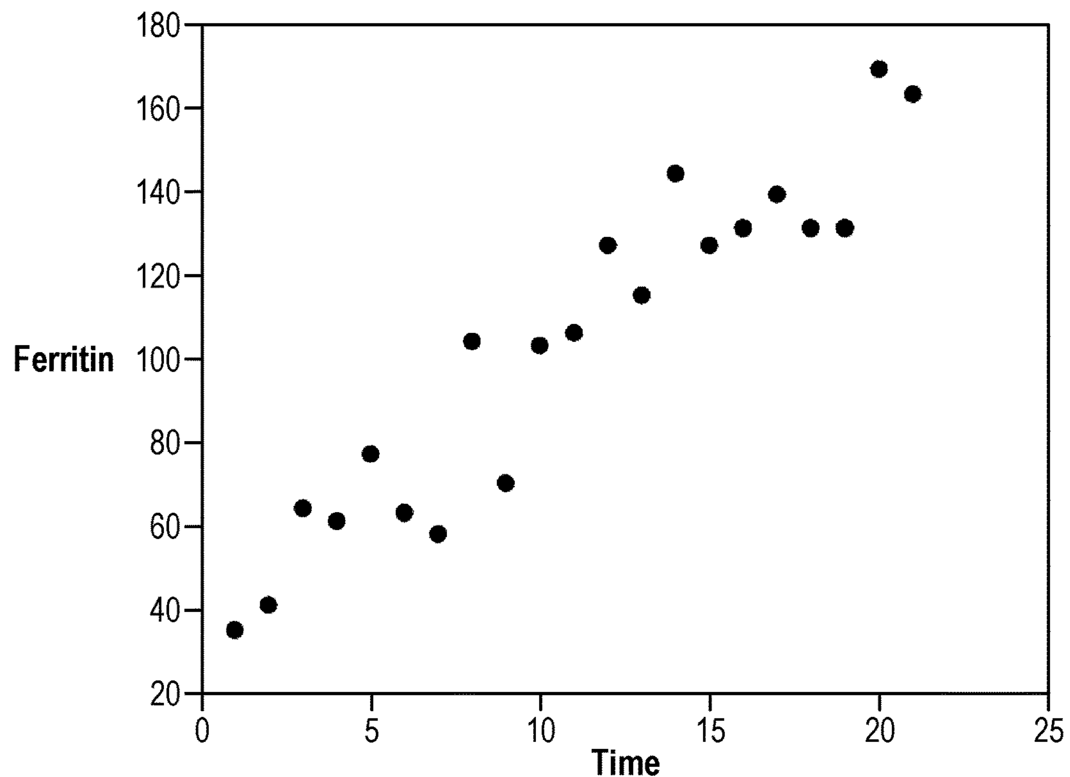
FIG. 17 illustrates an example of an abnormal series identified with method 2 for ferritin (increase of ferritin levels over the time)
Figure 18:
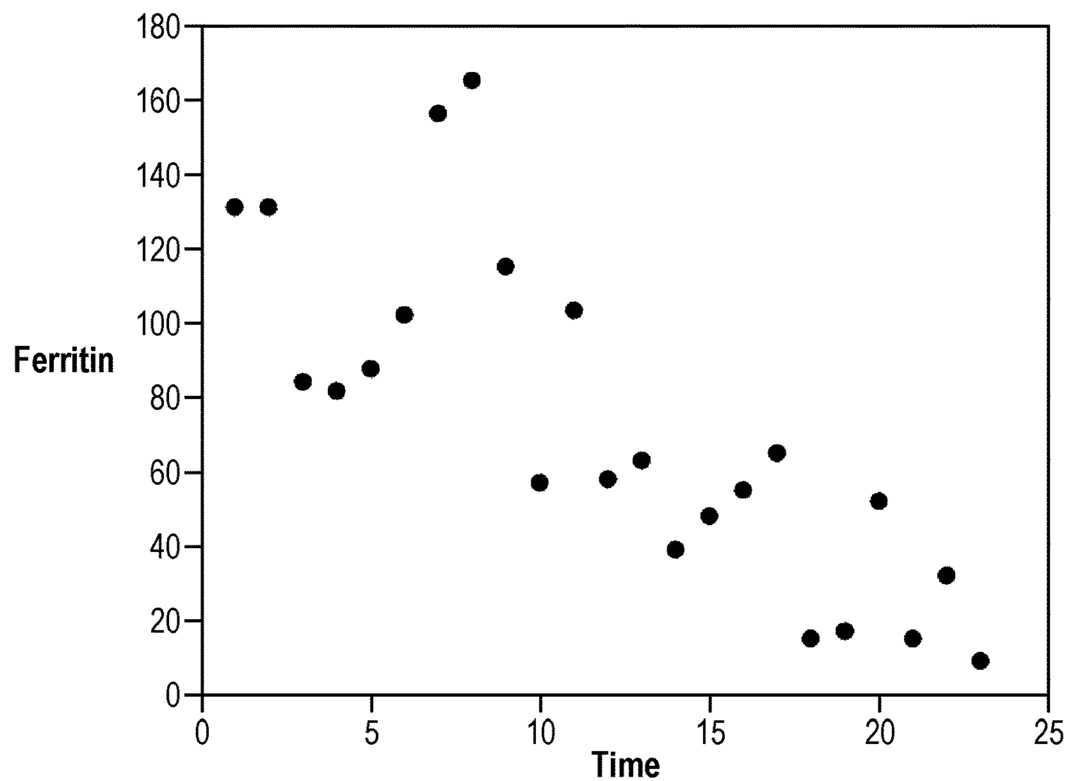
FIG. 18 illustrates an example of an abnormal series identified with method 2 for ferritin (decrease of ferritin levels over the time)

Results confirm those of the above analysis. A percentage of abnormal series close to that of false discovery rate is observed, except for ferritin/Method 2, for which the number of abnormal series is found unexpectedly high. (15.5% for $\alpha=5\%$). As shown for two typical cases depicted in FIGS. 17 and 18 ferritin levels are found to increase or to decrease as a function of time for several individuals of the tested population. In FIGS. 17 and 18, the x-axis corresponds to the indices of the samples, starting at x=1. The y-axis is the ferritin value in μmol/L.

Validation of Data

Data related to hemoglobin levels of 60 individuals (comprising at least 7 measures) randomly chosen were extracted from the base and independently analyzed by a medicine doctor (data not transformed with log) and by the methods of the invention (choosing a threshold as low as $\alpha=2.5$) for seeking abnormal profiles. The abnormal profiles identified by the doctor and those while using the methods of the invention 1, 2 or 3 were then compared.

The doctor spotted out 13 "abnormal" series (22% of "abnormal" series) of the 60 series:

four of the four series (100%) detected by method 1 are found in the doctor's list.

Six of the seven series (85.7%) detected by method 2 are found also in the doctor's list.

Five of the seven series (71.4%) detected by method 3 are in the doctor's list.

Then it can be inferred that methods 1, 2 and 3 are in line with the diagnostic of the doctor, and therefore can be used to detect abnormal series with good accuracy. A lower concordance rate is found between the doctor analysis and results identified by method 3, this might be explained by the fact that seasonality has not been considered by the doctor, but used in method 3.

The invention claimed is:

1. A method for monitoring a health event in a mammal, comprising detecting at least one abnormal value within a series of values related to at least one biomarker, said biomarker corresponding to a physiological parameter or to the level of any biological or chemical entity measured from a biological sample of said mammal, the series of values ($x_1$, $x_2$, . . . , $x_n$) related to said at least one biomarker being obtained from independent variables ($X_1$, $X_2$, . . . , $X_n$) normally distributed;

said method comprising the following steps of:

E1: determining from each biological sample collected at different periods of time from said mammal, a value related to said at least one biomarker thereby acquiring a series of values ($x_1$, $x_2$, . . . , $x_n$) related to said biomarker, E2: storing the series of values ($x_1$, $x_2$, . . . , $x_n$) on a database (DB) stored in a memory (12);

said method comprising the following steps run with a processor (14) that can retrieve data from the database (DB) in the memory:

E3: calculating, for the whole series of values of step E2 a single value $t_n$ of an indicator ($T_n$), said indicator ($T_n$) being based on a studentized form ($R_{n,i}$) of the variables ($X_1$, $X_2$, . . . , $X_n$), said calculation consisting of extracting the maximum observed value ($t_n$) of the studentized form ($R_{n,i}$) calculated for each value of the series of values ($x_1$, $x_2$, . . . , $x_n$), E4: comparing the observed value ($t_n$) of the indicator ($T_n$) to the quantile ($c_{a,n}$) of the distribution of ($T_n$) said quantile being stored in the memory, E5: if the observed value ($t_n$) of the indicator ($T_n$) is above the quantile, reporting, on displaying means (20), a presence of an abnormal value in the series thereby indicating the occurrence of a health event for said mammal;

wherein, when searching for one series of samples which comprises an abnormal value:

a single series $x_1$, $x_2$, . . . , $x_n$ of n values is stored on the database (DB), n is the number of variables, $X_1$, $X_2$, . . . , $X_n$ represent the n variables, the studentized form is a studentized residual expressed as:

$$R_{n,i} = \frac{X_i - \overline{X}_{n,-i}}{\hat{\sigma}_{n,-i}\sqrt{1 + \frac{1}{n-1}}}$$

the indicator $T_n$ is expressed as:

$$T_n = \max_{i\in\{1,\ldots,n\}} |R_{n,i}|$$

where $$\overline{X}_{n,-i} = \frac{1}{n-1}\sum_{k=1,k\neq i}^{n-1} X_k$$

$$\hat{\sigma}^2_{n,-i} = \frac{1}{n-2}\sum_{k=1,k\neq i}^{n-1} (X_k - \overline{X}_{n,-i})^2$$

the relevant table of quantiles of the distribution of $T_n$ is table 1;

or, in multivariate case, a single series $x_1$, $x_2$, . . . , $x_n$ of n values is stored on the database (DB), n is the number of variables of dimension d, $X_1$, $X_2$, . . . , $X_n$ are n independent $R^d$ valued random vectors, where $X_i \sim N(\mu_i, C)$ and C the covariance matrix is assumed to be invertible the studentized form is expressed as a normalized length of the residual vector:

$$R_{n,i} = \frac{n-1}{nd}(X_i - \overline{X}_{n,-i})' C^{-1}_{n,-i}(X_i - \overline{X}_{n,-i})$$

where the notation z' means the transpose of the vector Z, the indicator $T_n$ is expressed as:

$$T_n = \max_{i\in\{1,\ldots,n\}} R_{n,i}$$

where $$\overline{X}_{n,-i} = \frac{1}{n-1}\sum_{k=1,k\neq i}^{n-1} X_k$$

$$C_{n,-i} = \frac{1}{n-1-d}\sum_{k=1,k\neq i}^{n-1} (X_k - \overline{X}_{n,-i})(X_k - \overline{X}_{n,-i})'$$

and the relevant table of quantiles of the distribution of $T_n$ is for instance table 1 (for d=2 and d=3), or wherein, when searching for a series of consecutive observations that are abnormal compared to the rest of the series, a single series $x_1$, $x_2$, . . . , $x_n$ of n values is stored on the database (DB), n is the number of variables, $X_1$, $X_2$, . . . , $X_n$ represent the variables, $\varphi$ is the collection of all possible intervals I of consecutive integers included in $\{1, \ldots, n\}$ with length $1 \leq |I| < n$, $\{1, \ldots, n\} = I \cup \bar{I}$ and $I \cap \bar{I} = \emptyset$, the studentized form is expressed as:

$$R_{n,I} = \frac{X_I - X_{\bar{I}}}{\hat{\sigma}_{n,I}\sqrt{1 + \frac{1}{n-1}}}$$

the indicator $T_n$ is expressed as:

$$T_n = \max_{I \in \varphi} |R_{n,I}|$$

where $$\bar{X}_I = \frac{1}{|I|}\sum_{k \in I} X_k$$

$$\overline{X}_{\bar{I}} = \frac{1}{n - |I|}\sum_{k \in \bar{I}} X_k$$

$$\hat{\sigma}^2_{np} = \frac{1}{n-2}\left(\sum_{k \in I}(X_k - \bar{X}_{\bar{I}})^2 + \sum_{k \in \bar{I}}(X_k - \bar{X}_{\bar{I}})^2\right)$$

the relevant table of quantiles of the distribution of $T_n$ is for instance table 2, or wherein, when searching for an abnormal series when a sample is split in two subsamples of observations, two series of $n_1$ and $n_2$ values are stored on the database (DB), $x_1, x_2, \ldots, x_{n_1}$ and $y_1, y_2, \ldots, y_{n_2}$, the studentized forms are studentized residuals expressed as:

$$R_{n_1,i} = \frac{X_i - \bar{X}_{n_1,-i}}{\hat{\sigma}_{X,-i,Y}\sqrt{1 + \frac{1}{n_1 - 1}}}$$

and $$R_{n_2,j} = \frac{Y_j - \bar{Y}_{n_2,-j}}{\hat{\sigma}_{Y,-j,X}\sqrt{1 + \frac{1}{n_2 - 1}}}$$

the indicator $T_n$ is expressed as:

$$T_n = \max\left\{\max_{i \in \{1, \ldots, n_1\}} |R_{n_1,i}|, \max_{j \in \{1, \ldots, n_2\}} |R_{n_2,j}|\right\}$$

where $$\bar{X}_{n_1,-i} = \frac{1}{n_1 - 1}\sum_{k=1,k \neq i}^{n_1} X_k$$

$$\bar{Y}_{n_2,-j} = \frac{1}{n_2 - 1}\sum_{k=1,k \neq j}^{n_2} Y_k$$

$$\hat{\sigma}^2_{X,-i,Y} = \frac{1}{n-3}\left(\sum_{k=1,k \neq i}^{n_1}(X_k - \bar{X}_{n_1,-i})^2 + \sum_{k=1}^{n_2}(Y_k - \bar{Y}_{n_2})^2\right)$$

$$\hat{\sigma}^2_{Y,-j,X} = \frac{1}{n-3}\left(\sum_{k=1}^{n_1}(X_k - \bar{X}_{n_1})^2 + \sum_{k=1,k \neq j}^{n_2}(Y_k - \bar{Y}_{n_2,-j})^2\right)$$

and the relevant table of quantiles of the distribution of $T_n$ is for instance table 3, or, in a multivariate case, two series of $n_1$ and $n_2$ values are stored on the database (DB), $x_1, x_2, \ldots, x_{n_1}$ and $y_1, y_2, \ldots, y_{n_2}$, $-X_1, X_2, \ldots, X_{n_1}$ and $Y_1, Y_2, \ldots, Y_{n_2}$ represent the variables as two independent series of independent gaussian $R^d$ valued random vectors where $X_i \sim N(\mu_{X_i}, C)$, $Y_j \sim N(\mu_{Y_j}, C)$ and C, the covariance matrix, is assumed to be invertible, n is the number of variables of dimension d, the studentized form is expressed as a normalized length of the residual vector:

$$R_{n_1,i} = \frac{n_1 - 1}{n_1 d}(X_i - \bar{X}_{n_1,-i})' C^{-1}_{X,-i,Y}(X_i - \bar{X}_{n_1,-i})$$

$$R_{n_2,j} = \frac{n_2 - 1}{n_2 d}(Y_j - \bar{Y}_{n_2,-j})' C^{-1}_{Y,-j,X}(Y_j - \bar{Y}_{n_2,-i})$$

and the indicator $T_n$ is expressed as:

$$T_n = \max\left\{\begin{matrix}\max_{i \in \{1, \ldots, n_1\}} R_{n_1,i} \\ \max_{j \in \{1, \ldots, n_2\}} R_{n_2,j}\end{matrix}\right\}$$

where $$\bar{X}_{n_1,-i} = \frac{1}{n_1 - 1}\sum_{k=1,k \neq i}^{n_1} X_k$$

$$\bar{Y}_{n_2,-j} = \frac{1}{n_2 - 1}\sum_{k=1,k \neq j}^{n_2} Y_k$$

$$C_{X,-i,Y} = \frac{1}{n-2-d}\left(\sum_{k=1,k \neq i}^{n_1}(X_k - \bar{X}_{n_1,-i})(X_k - \bar{X}_{n_1,-i})' + \sum_{k=1}^{n_2}(Y_k - \bar{Y}_{n_2})(Y_k - \bar{Y}_{n_2})'\right)$$

$$C_{Y,-j,X} = \frac{1}{n-2-a}\left(\sum_{k=1}^{n_1}(X_k - \bar{X}_{n_1})(X_k - \bar{X}_{n_1})' + \sum_{k=1,k \neq j}^{n_2}(Y_k - \bar{Y}_{n_2,-j})(Y_k - \bar{Y}_{n_2,-j})'\right).$$

2. The method according to claim 1, comprising a further step of:

E6: identifying from the series of values reported in step E2 at least one value being considered as abnormal, and E7: reporting on displaying means (20) that at least one abnormal value.

3. The method according to claim 1, further comprising a step ES of running a Shapiro test on the stored values ($x_1, x_2, \ldots, x_{n_1}$) to check if the variables are normally distributed.

4. The method according to claim 1, further comprising a step ET of applying a function to the values to turn them into normally distributed variables, such as a log transformation.

5. The method according to claim 1, wherein the at least one biomarker represented by the series of values is chosen in the following list: ferritin, serum iron, hemoglobin, erythrocyte count, hematocrit levels, complete blood count, platelets, reticulocytes, soluble transferrin receptor, vitamin B9 in red blood cell, blood sugar, cholesterol, triglycerides, serum glutamic oxaloacetic transaminase (SGOT), serum glutamate pyruvate transaminase (SGPT), gamma-glutamyltransferase (γ-GT), lactate dehydrogenase (LDH), bilirubin, electrolytes (e.g. $Na^+$, $Cl^-$, $K^+$, $HCO3^-$, $Ca2^+$, $Mg2^+$), alkaline phosphatases Magnesium in red blood cells, creatinine, androstenedione, urea, uric acid, haptoglobin, C-reactive protein (CRP), transthyretin, orosomucoid, creatine phosphokinase (CPK), inorganic phosphate (PO4), thyroid-stimulating hormone (TSH), testosterone, cortisol, erythropoietin (EPO), ferritin, luteinizing hormone (LH), Insulin-like growth factor 1 (IGF-1), osteocalcin, calcifediol (25 OHD3).

6. A program for computer comprising code lines loaded on to a non-transitory computer readable medium and to be executed by a processor (14), said code lines being configured to operate a method according to claim 1 from its step E2 to E4.

7. A system for monitoring a health event in a mammal, comprising detecting at least one abnormal value within a series of values related to at least one biomarker, said biomarker corresponding to a physiological parameter or to the level of any biological or chemical entity measured from a biological sample of said mammal, the system comprising:

a database (DB) stored on a memory (12), the database comprising at least a series of values ($x_1, x_2, \ldots, x_n$) related to said at least one biomarker being obtained from independent variables ($X_1, X_2, \ldots, X_n$) normally distributed according to N ($\mu_x$, $\sigma^2$);

the values representing the evolution of the biomarker at different period of times, the values ($x_1, x_2, \ldots, x_n$) of the biomarker being obtained from independent variables ($X_1, X_2, \ldots, X_n$) normally distributed N ($\mu_X$, $\sigma^2$), a processor (14) comprising:

calculating means to calculate, for the whole series of values ($x_1, x_2, \ldots, x_n$) stored in the database (DB), a single value ($t_n$) of an indicator ($T_n$), said indicator ($T_n$) being based on a studentized form ($R_{n,i}$) of the variables ($X_1, X_2, \ldots, X_n$), said calculation consisting of extracting the maximum value ($t_n$) of the studentized residual form ($R_{n,i}$) calculated for each value of the series ($x_1, x_2, \ldots, x_n$), comparing means to compare the observed value ($t_n$) of the indicator ($T_n$) to the quantile ($c_{a,n}$) of the distribution of ($T_n$), instruction means to instruct displaying means to report, or reporting means to report on displaying means, a presence of an abnormal value in the series, if the observed value ($t_n$) of the indicator ($T_n$) is above the quantile, wherein, when searching for one series of samples which comprises an abnormal value:

a single series $x_1, x_2, \ldots, x_n$ of n values is stored on the database (DB), n is the number of variables, $X_1, X_2, \ldots, X_n$ represent the n variables, the studentized form is a studentized residual expressed as:

$$R_{n,i} = \frac{X_i - \bar{X}_{n,-i}}{\hat{\sigma}_{n,-i}\sqrt{1 + \frac{1}{n-1}}}$$

the indicator $T_n$ is expressed as:

$$T_n = \max_{i \in \{1, \ldots, n\}} |R_{n,i}|$$

-continued where $$\bar{X}_{n,-i} = \frac{1}{n-1}\sum_{k=1,k\neq i}^{n-1} X_k$$

$$\hat{\sigma}^2_{n,-i} = \frac{1}{n-2}\sum_{k=1,k\neq i}^{n-1} \left(X_k - \bar{X}_{n,-i}\right)^2$$

the relevant table of quantiles of the distribution of $T_n$ is table 1;

Or, in multivariate case, a single series $x_1, x_2, \ldots, x_n$ of n values is stored on the database (DB), n is the number of variables of dimension d, $X_1, X_2, \ldots, X_n$ are n independent $R^d$ valued random vectors, where $X_i \sim N(\mu_i, C)$ and C the covariance matrix is assumed to be invertible the studentized form is expressed as a normalized length of the residual vector:

$$R_{n,i} = \frac{n-1}{nd}\left(X_i - \bar{X}_{n,-i}\right)' C^{-1}_{n,-i}\left(X_i - \bar{X}_{n,-i}\right)$$

where the notation z' means the transpose of the vector Z, the indicator $T_n$ is expressed as:

$$T_n = \max_{i \in \{1, \ldots, n\}} R_{n,i}$$

where $$\bar{X}_{n,-i} = \frac{1}{n-1}\sum_{k=1,k\neq i}^{n-1} X_k$$

$$C_{n,-i} = \frac{1}{n-1-d}\sum_{k=1,k\neq i}^{n-1} \left(X_k - \bar{X}_{n,-i}\right)\left(X_k - \bar{X}_{n,-i}\right)'$$

and the relevant table of quantiles of the distribution of $T_n$ is for instance table 1 (for d=2 and d=3), Or wherein, when searching for a series of consecutive observations that are abnormal compared to the rest of the series, a single series $x_1, x_2, \ldots, x_n$ of n values is stored on the database (DB), n is the number of variables, $X_1, X_2, \ldots, X_n$ represent the variables, $\varphi$ is the collection of all possible intervals I of consecutive integers included in $\{1, \ldots, n\}$ with length $1 \leq |I| < n$, $\{1, \ldots, n\} = I \cup \bar{I}$ and $I \cap \bar{I} = \emptyset$, the studentized form is expressed as:

$$R_{n,I} = \frac{\bar{X}_I - \bar{X}_{\bar{I}}}{\hat{\sigma}_{n,I}\sqrt{1 + \frac{1}{n-1}}}$$

the indicator $T_n$ is expressed as:

$$T_n = \max_{I \in \varphi} |R_{n,I}|$$

-continued where $$\bar{X}_I = \frac{1}{|I|}\sum_{k\in I} X_k$$

$$\bar{X}_{\bar{I}} = \frac{1}{n-|I|}\sum_{k\in \bar{I}} X_k$$

$$\hat{\sigma}^2_{n,I} = \frac{1}{n-2}\left(\sum_{k\in I}(X_k - \bar{X}_I)^2 + \sum_{k\in \bar{I}}(X_k - \bar{X}_{\bar{I}})^2\right)$$

the relevant table of quantiles of the distribution of Tn is for instance table 2, or wherein, when searching for an abnormal series when a sample is split in two subsamples of observations, two series of $n_1$ and $n_2$ values are stored on the database (DB), $x_1, x_2, \ldots, x_{n_1}$ and $y_1, y_2, \ldots, y_{n_2}$, the studentized forms are studentized residuals expressed as:

$$R_{n_1,i} = \frac{X_i - \bar{X}_{n_1,-i}}{\hat{\sigma}_{X,-i,Y}\sqrt{1+\frac{1}{n_1-1}}}$$

and $$R_{n_2,j} = \frac{Y_j - \bar{Y}_{n_2,-j}}{\hat{\sigma}_{Y,-j,X}\sqrt{1+\frac{1}{n_2-1}}}$$

the indicator $T_n$ is expressed as:

$$T_n = \max\left\{\max_{i\in\{1,\ldots,n_1\}}|R_{n_1,i}|, \max_{j\in\{1,\ldots,n_2\}}|R_{n_2,j}|\right\}$$

where $$\bar{X}_{n_1,-i} = \frac{1}{n_1-1}\sum_{k=1,k\neq i}^{n_1} X_k$$

$$\bar{Y}_{n_2,-j} = \frac{1}{n_2-1}\sum_{k=1,k\neq j}^{n_2} Y_k$$

$$\hat{\sigma}^2_{X,-i,Y} = \frac{1}{n-3}\left(\sum_{k=1,k\neq i}^{n_1}(X_k - \bar{X}_{n_1,-i})^2 + \sum_{k=1}^{n_2}(Y_k - \bar{Y}_{n_2})^2\right)$$

$$\hat{\sigma}^2_{Y,-j,X} = \frac{1}{n-3}\left(\sum_{k=1}^{n_1}(X_k - \bar{X}_{n_1})^2 + \sum_{k=1,k\neq j}^{n_2}(Y_k - \bar{Y}_{n_2,-j})^2\right)$$

and the relevant table of quantiles of the distribution of $T_n$ is for instance table 3, or, in a multivariate case, two series of $n_1$ and $n_2$ values are stored on the database (DB), $x_1, x_2, \ldots, x_{n_1}$ and $y_1, y_2, \ldots, y_{n_2}$, -$X_1$, $X_2, \ldots, X_{n_1}$ and $Y_1, Y_2, \ldots, Y_{n_2}$ represent the variables as two independent series of independent gaussian $R^d$ valued random vectors where $X_i \sim N(\mu_{X_i}, C)$, $Y_j \sim N(\mu_{Y_j}, C)$ and C, the covariance matrix, is assumed to be invertible, n is the number of variables of dimension d, the studentized form is expressed as a normalized length of the residual vector:

$$R_{n_1,i} = \frac{n_1-1}{n_1 d}(X_i - \bar{X}_{n_1,-i})' C^{-1}_{X,-i,Y}(X_i - \bar{X}_{n_1,-i})$$

$$R_{n_2,j} = \frac{n_2-1}{n_2 d}(Y_j - \bar{Y}_{n_2,-j})' C^{-1}_{Y,-j,X}(Y_j - \bar{Y}_{n_2,-i})$$

and the indicator $T_n$ is expressed as:

$$T_n = \max\left\{\begin{matrix}\max_{i\in\{1,\ldots,n_1\}} R_{n_1,i} \\ \max_{j\in\{1,\ldots,n_2\}} R_{n_2,j}\end{matrix}\right\}$$

where $$\bar{X}_{n_1,-i} = \frac{1}{n_1-1}\sum_{k=1,k\neq i}^{n_1} X_k$$

$$\bar{Y}_{n_2,-j} = \frac{1}{n_2-1}\sum_{k=1,k\neq j}^{n_2} Y_k$$

$$C_{X,-i,Y} = \frac{1}{n-2-d}\left(\sum_{k=1,k\neq i}^{n_1}(X_k - \bar{X}_{n_1,-i})(X_k - \bar{X}_{n_1,-i})' + \sum_{k=1}^{n_2}(Y_k - \bar{Y}_{n_2})(Y_k - \bar{Y}_{n_2})'\right)$$

$$C_{Y,-j,X} = \frac{1}{n-2-d}\left(\sum_{k=1}^{n_1}(X_k - \bar{X}_{n_1})(X_k - \bar{X}_{n_1})' + \sum_{k=1,k\neq j}^{n_2}(Y_k - \bar{Y}_{n_2,-j})(Y_k - \bar{Y}_{n_2,-j})'\right).$$

8. Use of a method according to claim 1 for detecting a potential doping issue.

9. Use of a method according to claim 1 wherein monitoring a health event comprises detecting any potential health issue of the individual, in order to launch further investigations.

10. Use of a program according to claim 6 for detecting a potential doping issue.

11. Use of a system according to claim 7 for detecting a potential doping issue.

12. Use of a program according to claim 6 wherein monitoring a health event comprises detecting any potential health issue of the individual, in order to launch further investigations.

13. Use of a system according to claim 7 wherein monitoring a health event comprises detecting any potential health issue of the individual, in order to launch further investigations.

* * * * *